United States Patent
Yao et al.

(10) Patent No.: US 11,982,803 B2
(45) Date of Patent: May 14, 2024

(54) PATHOLOGIC MICROSCOPE, DISPLAY MODULE, CONTROL METHOD AND APPARATUS, AND STORAGE MEDIUM

(71) Applicant: TENCENT TECHNOLOGY (SHENZHEN) COMPANY LIMITED, Guangdong (CN)

(72) Inventors: Jianhua Yao, Shenzhen (CN); Xiao Han, Shenzhen (CN); Junzhou Huang, Shenzhen (CN); Wei Liu, Shenzhen (CN); Yen-Hsiang Wang, Shenzhen (CN); De Cai, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 871 days.

(21) Appl. No.: 17/016,521

(22) Filed: Sep. 10, 2020

(65) Prior Publication Data

US 2020/0409134 A1    Dec. 31, 2020

Related U.S. Application Data

(63) Continuation of application No. PCT/CN2019/100147, filed on Aug. 12, 2019.

(30) Foreign Application Priority Data

Aug. 21, 2018   (CN) .......................... 201810956223.3

(51) Int. Cl.
*G06N 20/00*   (2019.01)
*G01N 33/574*   (2006.01)
(Continued)

(52) U.S. Cl.
CPC ......... *G02B 21/365* (2013.01); *G01N 33/574* (2013.01); *G06T 7/0012* (2013.01); *G06T 2207/30096* (2013.01)

(58) Field of Classification Search
USPC ....... 382/100–228; 600/300–561; 704/1–275
See application file for complete search history.

(56) References Cited

U.S. PATENT DOCUMENTS

2015/0160448 A1   6/2015   Hong et al.
2018/0150605 A1*  5/2018   Co ....................... G10L 15/063
(Continued)

FOREIGN PATENT DOCUMENTS

CN        101902950 A    12/2010
CN        104280886 A     1/2015
(Continued)

OTHER PUBLICATIONS

Gainer C Romanowski; Augmented Stereoscopic Microscope For Improving Image Guidance During Surgical Intervention Has Augmentation Module That Combines Synthetic Images With Visible Bright-field Images To Form Co-registered Augmented Images; Aug. 16, 2018 (Year: 2016).*

(Continued)

*Primary Examiner* — Marcellus J Augustin
(74) *Attorney, Agent, or Firm* — Sughrue Mion, PLLC

(57) ABSTRACT

An apparatus, method and storage medium for controlling a pathologic microscope are provided. The method includes obtaining a pathological digital image from an incident optical path of the pathologic microscope; performing artificial intelligence (AI) analysis on the pathological digital image to generate AI analysis information; and controlling an augmented reality (AR) projection component to project the AI analysis information on a microscopic field of the pathologic microscope on an outgoing optical path.

16 Claims, 15 Drawing Sheets

(51) Int. Cl.
  *G02B 21/34* (2006.01)
  *G02B 21/36* (2006.01)
  *G06T 7/00* (2017.01)

(56) References Cited

U.S. PATENT DOCUMENTS

| | | | | |
|---|---|---|---|---|
| 2019/0336063 A1* | 11/2019 | Dascalu | ............... | A61B 5/0064 |
| 2020/0097727 A1* | 3/2020 | Stumpe | ............... | G02B 21/361 |
| 2021/0166380 A1* | 6/2021 | Yip | ..................... | G06V 20/698 |

FOREIGN PATENT DOCUMENTS

| | | | |
|---|---|---|---|
| CN | 104965302 A | 10/2015 | |
| CN | 107578808 A | 1/2018 | |
| CN | 109031643 A | 12/2018 | |
| CN | 110007455 A | 7/2019 | |
| EP | 2950130 A1 | 12/2015 | |
| JP | 200671430 A | 3/2006 | |
| JP | 2006297060 A | 11/2006 | |
| KR | 101889725 B1 | 8/2018 | |
| WO | 2016/130424 A1 | 8/2016 | |
| WO | 2018001689 A1 | 1/2018 | |
| WO | 2018116851 A1 | 6/2018 | |

OTHER PUBLICATIONS

Extended European Search Report dated Jan. 14, 2022 from the European Patent Office in EP Application No. 19851573.6.
Communication dated Feb. 1, 2022 from the European Patent Office in EP Application No. 19851573.6.
Translation of Written Opinion dated Nov. 20, 2019, issued by the International Searching Authority in application PCT/CN2019/100147.
Communication dated Sep. 27, 2021, issued by the Japanese Patent Office in application No. 2020-549545.
Written Opinion of the International Searching Authority of PCT/CN2019/100147 dated Nov. 20, 2019 (PCT/ISA/237).
Chinese Office Action of CN 201810956223.3 dated Feb. 3, 2020.
International Search Report of PCT/CN2019/100147 dated Nov. 20, 2019 [PCT/ISA/210].
Yuhan Liu, et al.,"Multi-View Learning and Deep Learning for Microscopic Neuroblastoma Pathology Image Diagnosis", PRICAI, 2018, pp. 545-558 (14 pages).
European Office Action dated Dec. 11, 2023 in Application No. 19 851 573.6.

* cited by examiner

PATHOLOGIC MICROSCOPE, DISPLAY MODULE, CONTROL METHOD AND APPARATUS, AND STORAGE MEDIUM

CROSS-REFERENCE TO RELATED APPLICATION(S)

This application is a continuation of PCT/CN2019/100147, filed on Aug. 12, 2019, and claims priority to Chinese Patent Application No. 201810956223.3, entitled "PATHOLOGIC MICROSCOPE, DISPLAY MODULE, CONTROL METHOD AND APPARATUS, AND STORAGE MEDIUM," filed with the China National Intellectual Property Administration on Aug. 21, 2018, the disclosures of which are incorporated by reference herein in their entireties.

BACKGROUND

1. Field

Embodiments of the disclosure relate to the field of microscope imaging, and in particular, to a pathologic microscope, a display module, a control method and apparatus, and a storage medium.

2. Description of Related Art

Pathological examination is a pathomorphological method used for examining pathologic changes in organs, tissues, or cells of a body. In the process of pathological examination, a doctor may cut a lesion tissue of a specific size, make a pathological section by adopting a pathologic histology method, and then observe the pathological section by using a pathologic microscope to observe a lesion. In the related art, a pathological digital image of a pathological section may be obtained, and a doctor determines whether a suspicious lesion area exists through the pathological digital image, and if so, the suspicious lesion area may be confirmed again in a pathological section image of a microscope field. The suspicious lesion area may be found in the microscope field only by switching to the microscope field, which takes a certain time, and therefore the pathologic microscope is inconvenient in terms of real-time performance in an observation process.

SUMMARY

According to an embodiment, there is provided an apparatus for controlling a pathologic microscope, the apparatus including: an image acquisition component disposed on an incident optical path of the pathologic microscope and configured to acquire a pathological digital image from the incident optical path; a control component configured to perform artificial intelligence (AI) analysis on the pathological digital image to generate AI analysis information; and an augment reality (AR) projection component disposed on an outgoing optical path of the pathologic microscope and configured to project the AI analysis information on a microscopic field of the pathologic microscope on the outgoing optical path.

According to an embodiment, there is provided a method for controlling a pathologic microscope, the method including: obtaining a pathological digital image from an incident optical path of the pathologic microscope; performing artificial intelligence (AI) analysis on the pathological digital image to generate AI analysis information; and controlling an augmented reality (AR) projection component to project the AI analysis information on a microscopic field of the pathologic microscope on an outgoing optical path.

According to an embodiment, there is provided a non-transitory computer-readable storage medium storing computer program code to cause at least one computer processor to: obtain a pathological digital image from an incident optical path of a pathologic microscope; perform artificial intelligence (AI) analysis on the pathological digital image to generate AI analysis information; and control an augmented reality (AR) projection component to project the AI analysis information on a microscopic field of the pathologic microscope on an outgoing optical path.

Details of one or more embodiments of the disclosure are provided in the following description in conjunction with the accompanying drawings. Additional aspects, features, and advantages of the disclosure will become more apparent from the following description.

BRIEF DESCRIPTION OF THE DRAWINGS

To describe the embodiments of the disclosure more clearly, the following briefly introduces the accompanying drawings, which illustrate example embodiments of the disclosure. These and other aspects, features and advantages will become apparent from the following detailed description of example embodiments, which is to be read in conjunction with the accompanying drawings, in which.

DESCRIPTION

To make the objectives, technical solutions, and advantages of the disclosure clearer, the following further describes the embodiments of the disclosure in detail with reference to the accompanying drawings.

A pathologic microscope is widely used in clinical diagnosis and scientific research. The pathomorphology features of organs, tissues, or cells of a body may be obtained through pathological section images, so that the cause, pathogenesis, and development process of pathological changes can be clarified, and the pathological tissues can be evaluated and diagnosed. In traditional pathological diagnosis, a pathological section is analyzed and diagnosed by a professional doctor under a pathologic microscope.

Viewing a large quantity of pathological section images is a heavy task and some tasks are highly repetitive. For example, when counting cells in a pathological section image, a doctor easily makes wrong judgment due to fatigue and is more prone to error. By applying an artificial intelligence (AI) technology to the analysis of the pathological section image, the diagnosis of the doctor may be assisted.

Figure 1:
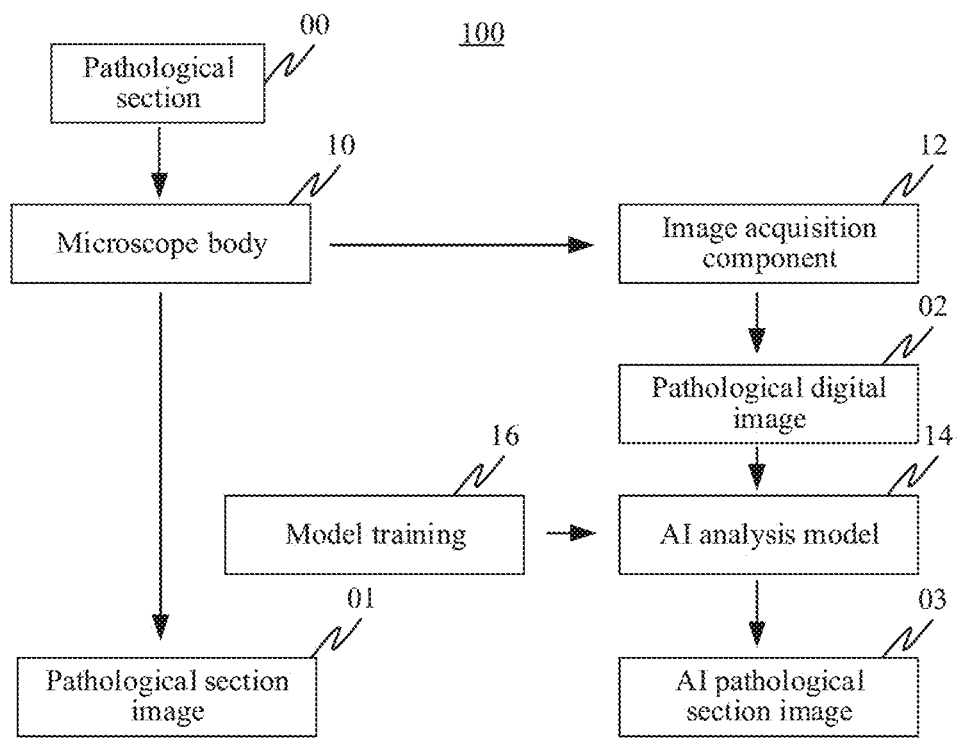
FIG. 1 is a diagram of a working principle of a pathologic microscope of a related art.

FIG. 1 is a diagram of a working principle of a pathologic microscope 100 according to the related art. The pathologic microscope 100 includes a microscope body 10 including an optical structure, and the microscope body 10 observes a pathological section 00 to obtain a pathological section image 01. In addition, the pathologic microscope 100 further includes an image acquisition component 12 and an AI analysis model 14. The image acquisition component 12 is configured to acquire a pathological digital image 02 of the pathological section 00 from an optical path of the microscope body 10, and the AI analysis model 14 is configured to perform algorithm analysis on the pathological digital image 02 to obtain an AI pathological section image 03. The AI pathological section image 03 may be displayed by using a liquid crystal display (LCD). However, a display is not limited thereto, and may include other types of displays.

During application of such an AI technology, a digital image needs to be first obtained from a pathologic microscope and then the digital image is analyzed through an AI algorithm. However, in the pathologic microscope 100 according to the related art, an image in a microscopic field is separated from an image processed by an AI algorithm, and a doctor needs to switch a visual field back and forth during entire observation of a pathological section image. Therefore, it does not allow a doctor or other medical practitioners to directly observe a pathological section under the pathologic microscope, and does not provide convenience for the doctor or medical practitioners.

In some embodiments, an AR technology is expected to be integrated into the pathologic microscope. A pathological section is directly analyzed in the microscopic field on the pathologic microscope, the pathological section is analyzed through the AI technology and corresponding AI analysis information is generated, and then the AI analysis information is directly integrated into the microscopic field of the pathologic microscope through the AR technology.

Figure 2:
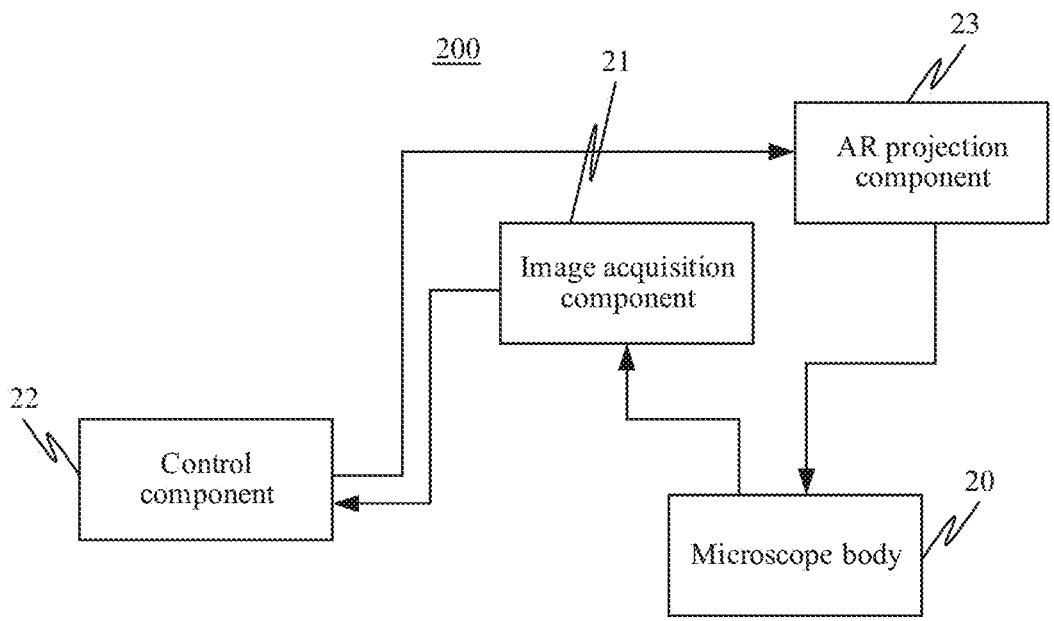
FIG. 2 is a schematic structural diagram of a pathologic microscope according to an embodiment.

FIG. 2 is a schematic structural diagram of a pathologic microscope 200 according to an exemplary embodiment. The pathologic microscope 200 includes a microscope body 20, an image acquisition component 21, a control component 22, and an AR projection component 23.

An incident optical path and an outgoing optical path are formed on the microscope body 20, the image acquisition component 21 is disposed on the incident optical path, an input end of the control component 22 is electrically connected to the image acquisition component 21, an output end of the control component 22 is electrically connected to the AR projection component 23, and the AR projection component 23 is disposed on the outgoing optical path.

An optical system on the microscope body 20 includes an objective lens, an eyepiece, a reflector, a condenser, and the like, and a structure of the optical system on the microscope body 20 is not limited to this embodiment. At least one of the lenses or reflectors forms the incident optical path and the outgoing optical path. In some embodiments, an optical path close to the objective lens is the incident optical path and an optical path close to the eyepiece is the outgoing optical path.

In some embodiments, the microscope body 20 includes a first body part corresponding to the incident optical path and a second body part corresponding to the outgoing optical path. In a possible implementation, the image acquisition component 21 is integrated into the first body part and the AR projection component 23 is integrated into the second body part. In another possible implementation, a first physical interface is formed on the first body part, a first physical connector is formed on the image acquisition component 21, and the first physical connector of the image acquisition component 21 is connected to the first physical interface of the first body part. Correspondingly, a second physical interface may be formed on the second body part, a second physical connector may be formed on the AR projection component 23, and the second physical connector of the AR projection component 23 may be connected to the second physical interface of the second body part. For example, the first physical interface and the second physical interface are at least one of a threaded interface, a socket, or a clamp interface.

The image acquisition component 21 is configured to acquire a pathological digital image from the incident optical path.

The control component 22 is configured to perform AI analysis on the pathological digital image to generate AI analysis information. The AI analysis information is information obtained by analyzing the pathological digital image by using an AI analysis model.

The AI analysis model may be stored in the control component 22 and may be configured to perform the AI analysis on the pathological digital image. In a possible embodiment, the control component 22 is further configured to obtain at least one AI analysis model, determine a target AI analysis model corresponding to a use scenario of the pathological digital image, and invoke the target AI analysis model to perform the AI analysis on the pathological digital image to generate the AI analysis information.

Different AI analysis models may have different analysis capabilities, and one or more AI analysis models may be disposed or stored in the control component 22 to be used. For example, at least one of a tumor area detection AI model, a cell detection AI model, or an infectious disease detection AI model may be simultaneously disposed in the control component 22.

The control component 22 is further configured to determine the tumor area detection AI model as the target AI analysis model in a case that the use scenario of the pathological digital image is tumor area detection, and invoke the tumor area detection AI model to perform the AI analysis on the pathological digital image to obtain tumor analysis information. In addition, the tumor analysis information may include any one of breast cancer analysis information, bone cancer analysis information, and digestive tract cancer analysis information. However, the tumor analysis information is not limited thereto, and may include any other information that may be relevant to the tumor analysis.

The control component 22 is further configured to determine the cell detection AI model as the target AI analysis model in a case that the use scenario of the pathological digital image is cell detection, and invoke the cell detection AI model to perform the AI analysis on the pathological digital image to obtain cell detection information. In addition, the cell detection information may include any one of cell count information, mitotic cell detection information, and cell nuclear detection information. However, the cell detection information is not limited thereto, and may include any other information that may be relevant to the cell detection.

The control component 22 is further configured to determine the infectious disease detection AI model as the target AI analysis model in a case that the use scenario of the pathological digital image is infectious disease detection, and invoke the infectious disease detection AI model to perform the AI analysis on the pathological digital image to obtain infectious disease detection information. In addition, the infectious disease detection information may include any one of plasmodium egg detection information and acid-fast bacilli detection information. However, the infectious disease detection information is not limited thereto, and may include any other information that may be relevant to the infectious disease.

In some embodiments, the control component 22 further downloads an AI analysis model from other devices on a local area network or a wide area network. For example, the control component 22 downloads the AI analysis model from the other devices according to a current use scenario.

The control component 22 is further configured to send the pathological digital image to a server. The server may store an AI analysis model and configured to perform the AI analysis on the pathological digital image by using the AI analysis model to obtain the AI analysis information. The control component 22 is further configured to receive the AI analysis information sent by the server. The server may be a server, a server cluster including a plurality of servers, or a cloud server running on a cloud.

The AR projection component 23 is configured to project the AI analysis information into a microscopic field of the microscope body 20 on the outgoing optical path. In some embodiments, the AI analysis information includes at least one of a text, a curve, a background color, or an animation. When the AI analysis information is superimposed as an image (or a picture) in the microscopic field, an AI pathological image (or an AI pathological picture) can be formed. For example, a region of interest may be marked in the AI pathological image, and may be marked through an arrow, a text, or the like. Alternatively, a region of interest may be marked by using a hot spot map.

According to the pathologic microscope provided in this embodiment, an image acquisition component acquires a pathological digital image, a control component performs AI analysis on the pathological digital image to obtain AI analysis information, and an AR projection component projects the AI analysis information into a microscopic field of a microscope body, so that a doctor can directly observe a pathological section image and the AI analysis information in the microscopic field at the same time, and does not need to switch a visual field back and forth in the entire observation process. The AI analysis information presented in this way may make the observation process of the pathologic microscope simpler and more direct, thereby allowing users to achieve a high real-time performance of the pathologic microscope in the use process.

In an embodiment based on FIG. 2, two disposing manners of the image acquisition component 21 are shown as examples for disposing the image acquisition component on the incident optical path of the microscope body 20.

Figure 3:
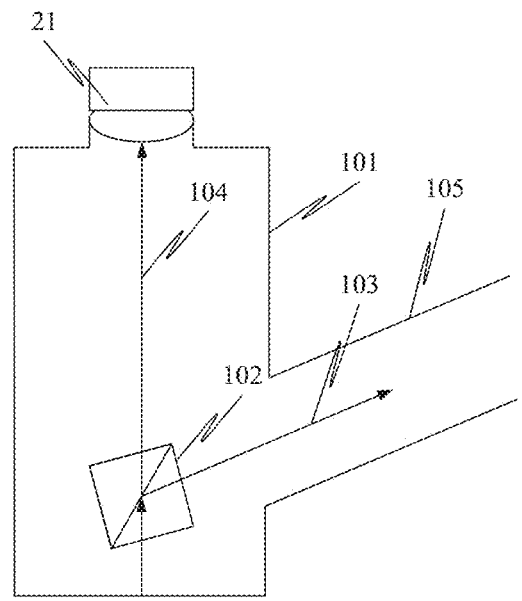
FIG. 3 is a schematic structural diagram of an image acquisition component disposed at a top end of a pathologic microscope according to an embodiment.

As shown in FIG. 3, a top end of an objective tube 101 of the microscope body 20 is embedded with an image acquisition component 21, and an incident light is split into one outgoing light 103 (refracted at a certain angle) through a beam splitter prism 102 to enter an eyepiece tube 105. At the same time, the incident light 104 passes through the beam splitter prism 102 to the top end of the objective tube 101. The image acquisition component 21 acquires the incident light 104 that passes through the beam splitter 102, and the incident light 104 represents a picture or an image observed by the microscope body 20.

Figure 4:
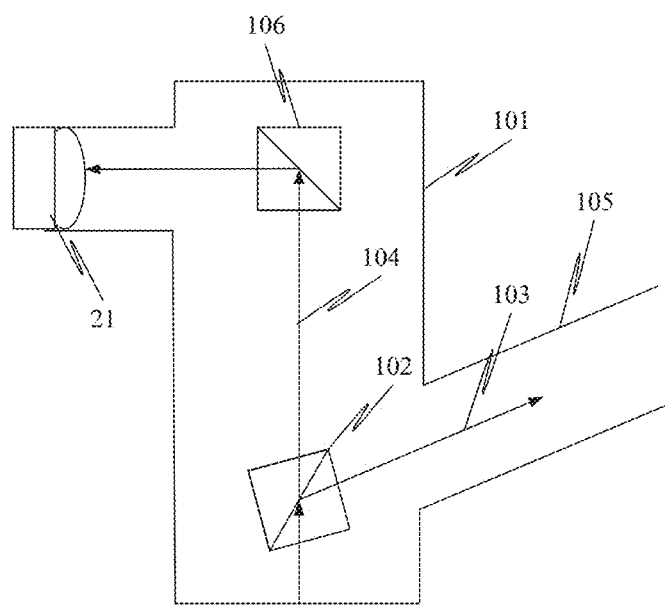
FIG. 4 is a schematic structural diagram of an image acquisition component disposed at a side end of a pathologic microscope according to an embodiment.

As shown in FIG. 4, a side end of an objective tube 101 of the microscope body 20 is embedded with an image acquisition component 21, and an incident light is split into one outgoing light 103 refracted by the beam splitter prism 102 to enter an eyepiece tube 105 and the incident light 104 that is transmitted to the top end of the objective tube 101 through the beam splitter prism 102. The incident light 104 that passes through the beam splitter is then reflected at the top end of the objective tube 101 by using a reflecting mirror 106. The reflected incident light 104 is then transmitted to the image acquisition component 21, and the image acquisition component 21 acquires the incident light 104 which represents a picture or an image observed by the microscope body 20.

The disposing manners of the image acquisition component 21 are merely examples for description, but the disposing manners of the image acquisition component 21 are not limited to this embodiment.

In the embodiment based on FIG. 2, two projection principles of an AR projection component are shown as examples for disposing the AR projection component on the outgoing optical path of the microscope body 20.

Figure 5:
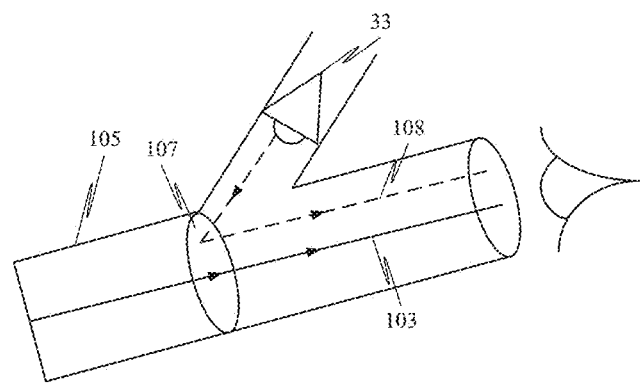
FIG. 5 is a first schematic structural diagram of an AR projection component of a pathologic microscope according to an embodiment.

As shown in FIG. 5, one side of an eyepiece tube 105 of the microscope body 20 is embedded with an AR projection component 33, where an embedding direction of the AR projection component 33 is opposite to the eyes of a user. Here, the AR projection component 33 generates a projection content 108 which is deflected by a lens 107 in the eyepiece tube 105, so that the deflected projection content 108 is parallel to an outgoing light 103, and the outgoing light 103 is a picture observed by the microscope body 20. The deflected projection content 108 and the outgoing light 103 are superimposed as an AR pathological image (or AR pathological picture).

Figure 6:
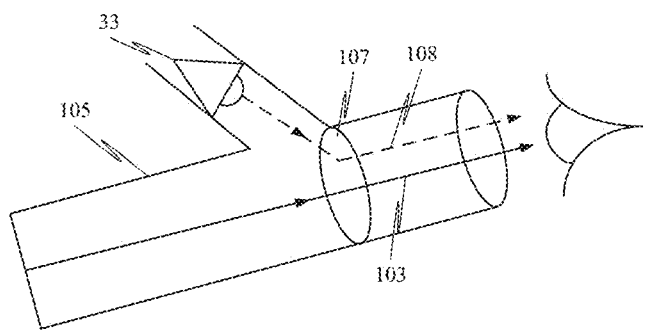
FIG. 6 is a second schematic structural diagram of an AR projection component of a pathologic microscope according to an embodiment.

As shown in FIG. 6, one side of an eyepiece tube 105 of the microscope body 20 is embedded with an AR projection component 33, an embedding direction of the AR projection component 33 is in a direction toward the eyes of a user. Here, the AR projection component 33 generates the projection content 108 which is refracted by a lens 107 in the eyepiece tube 105, and the refracted projection content 108 becomes parallel to the outgoing light 103. The outgoing light 103 is a picture observed by the microscope body 20. The refracted projection content 108 and the outgoing light 103 are superimposed as an AR pathological image (or AR pathological picture).

In some other embodiments, a speech interaction function may be included in the pathologic microscope. On one hand, a doctor may select and control corresponding functional modules in the pathologic microscope in a speech interaction manner. On the other hand, the pathologic microscope may further provide AI analysis information to the doctor in a prompt speech. For example, the pathologic microscope prompts a region of interest in a pathological section image to the doctor in a speech so that the doctor or a user may easily identify and view the region of interest. In addition, oral content of the doctor by be further converted into a pathological diagnosis report or into an electronic case history of a patient by using the speech interaction function.

Figure 7:
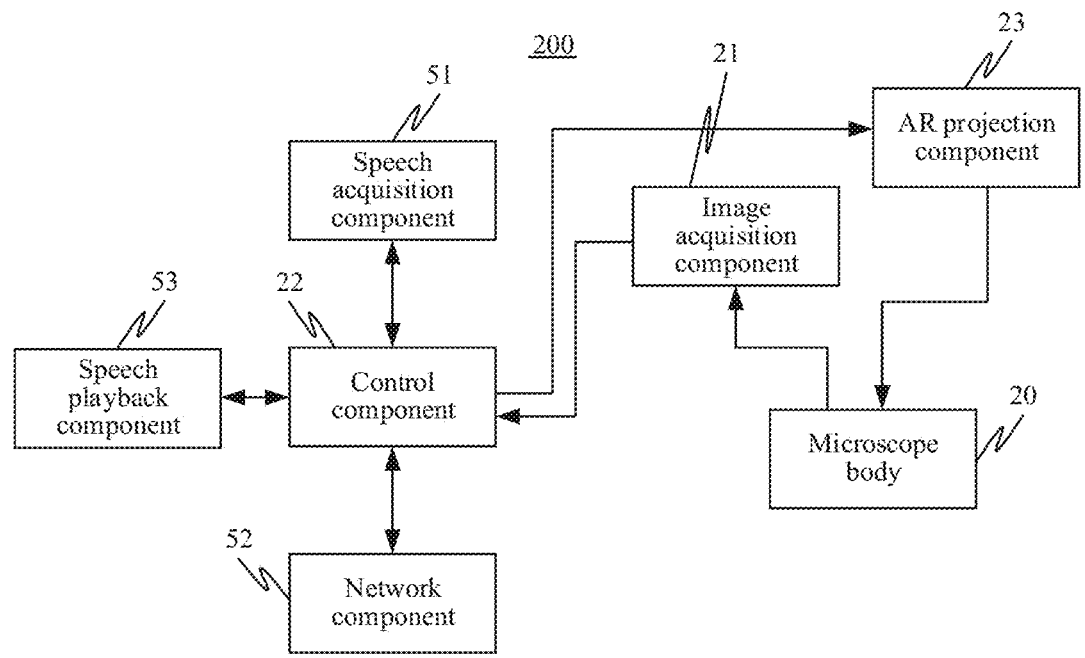
FIG. 7 is a schematic structural diagram of a pathologic microscope according to an embodiment.

FIG. 7 is a schematic structural diagram of a pathologic microscope 200 according to another exemplary embodiment. Here, in addition to the pathologic microscope 200 shown in FIG. 2, the pathologic microscope 200 further includes a speech acquisition component 51 connected to the control component 22.

The speech acquisition component 51 is configured to acquire an external speech signal. The control component 22 is configured to recognize a control instruction of the speech signal and control an analysis process of AI analysis according to the control instruction.

A microphone may be used as the speech acquisition component 51 to acquire an external speech signal and send the speech signal to the control component 22. The control component 22 recognizes content of the speech signal, and when the recognized content conforms to a preset control keyword, a corresponding control instruction may be received. The control component 22 performs a corresponding control operation on the pathologic microscope 200 through the control instruction. In some embodiments, a speech recognition engine is disposed in the control component 22, and the speech signal is recognized by using the speech recognition engine.

In a case that the control instruction is a model selection instruction, a target AI analysis model is selected according to the model selection instruction. For example, the target AI analysis model includes a tumor area detection AI model, a cell detection AI model, and an infectious disease detection AI model. According to an actual use scenario, a user inputs a speech signal to the control component 22 by using the microphone 51, and the control component 22 recognizes the speech signal to obtain a control instruction. In a case that the control instruction is a model selection instruction, the control component 22 selects, according to the model selection instruction, a target AI analysis model corresponding to the actual use scenario.

For example, when a doctor speaks "Select a tumor detection model" to the microphone 51, the speech recognition engine recognizes the sentence to obtain a recognition result. When the control component 22 determines that "tumor detection model" is consistent with a preset keyword in the recognition result, it is determined that a control instruction is received. The control instruction is a model selection instruction, and controls to select a locally stored tumor area detection AI model for detection.

In some embodiments, in a case that the control instruction is a first generation instruction, the control component 22 generates a pathological report according to the first generation instruction, the pathological report including AI analysis information.

The pathological report is a report formed after a doctor inputs oral content through the microphone 51 according to the AI analysis information. For example, the AI analysis information includes appearance information of a pathological tissue and lesion information of a pathological cell, and the oral content includes pathological diagnosis of a doctor.

In some embodiments, a case history report is generated in a case that the control instruction is a second generation instruction. The case history report may include the AI analysis information and patient information, and the patient information may be recognized from a text or a graphic code on a pathological section, or inputted by the doctor by using the speech acquisition component.

Figure 8:
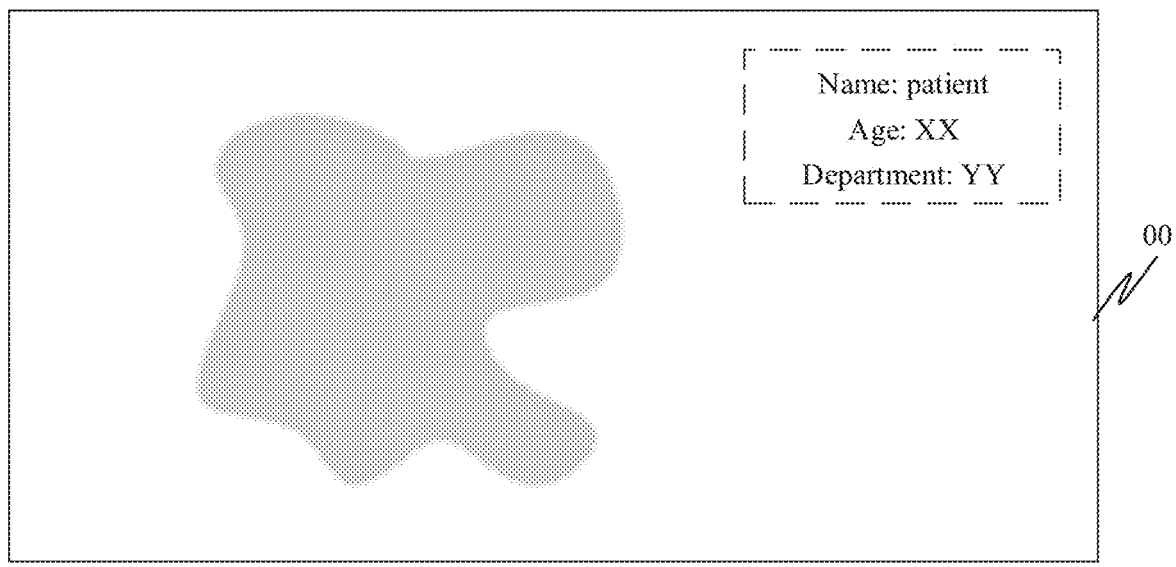
FIG. 8 is a schematic diagram of patient information in text recognized by a pathologic microscope according to an embodiment.

The patient information is recognized from a text on a pathological section 00. As shown in FIG. 8, for example, the patient information includes name, age, and visit department. The patient information may further include other information, and the patient information is not limited hereto.

Figure 9:
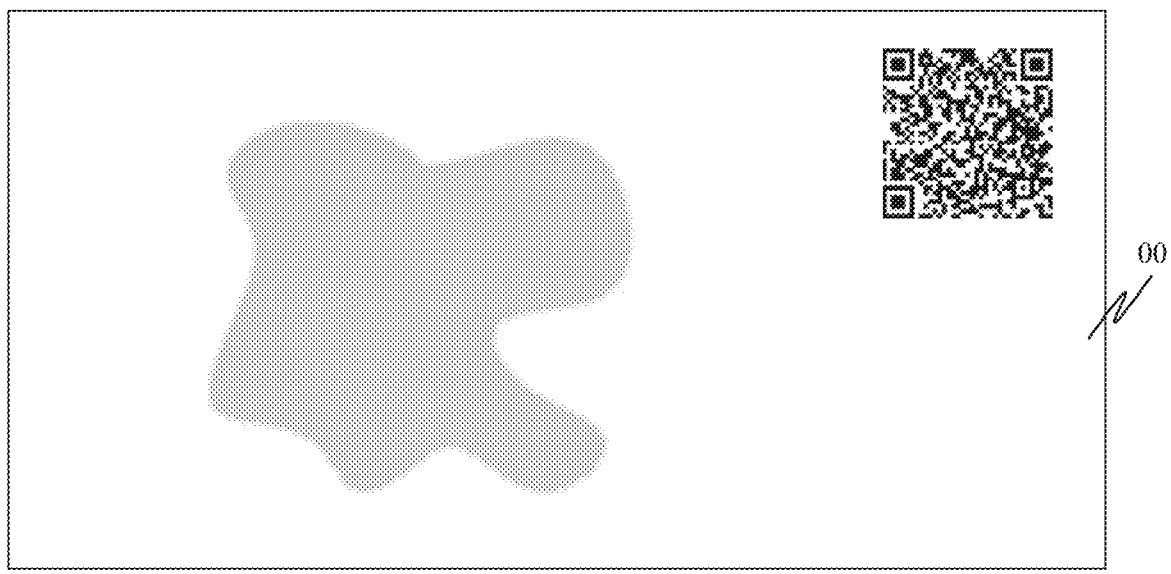
FIG. 9 is a schematic diagram of patient information in a QR code recognized by a pathologic microscope according to an embodiment.

The patient information may be recognized from a graphic code on the pathological section 00, such as a bar code or a QR code. As shown in FIG. 9, the control component 22 obtains corresponding patient information through a QR code being captured by the image acquisition component 21. The image acquisition component unit 21 may include a camera configured to capture an image.

Furthermore, the patient information may include name, gender, age, or occupation. However, this is not specifically limited to this embodiment.

In some embodiments, the control component 22 is further configured to recognize text content from the speech signal and generate a doctor record in the pathological report or the case history report according to the text content. The control component 22 recognizes a speech signal, and expresses content of the speech signal in a text form corresponding to the speech signal.

For example, a doctor first dictates pathological diagnosis through the microphone 51, the control component 22 recognizes dictated content and expresses the dictated content in a text form, the doctor may then give a speech signal of generating a pathological report. Accordingly, the control component 22 recognizes the speech signal of the doctor to form a control instruction, the control instruction is a first generation instruction, and the pathologic microscope 200 generates the pathological report. Alternatively, a doctor first dictates doctor diagnosis through the microphone 51, the control component 22 recognizes dictated content and expresses the dictated content in a text form to improve case history report content, the doctor then gives a speech signal of generating a case history report. Accordingly, the control component 22 recognizes the speech signal of the doctor to form a control instruction, the control instruction is a second generation instruction, and the pathologic microscope 200 generates the case history report.

In some embodiments, the pathologic microscope 200 further includes a network component 52 connected to the control component 22.

When a user inputs a control command to the control component 22 through the microphone 51, the control component 22 forms a control instruction to control the network component 52.

In a case that the control instruction is a model download instruction, the control component 22 downloads at least one AI analysis model using the network component 52, or in a case that a target AI analysis model is not stored, the control component 22 automatically downloads the target AI analysis model using the network component 52. For example, a user may input an instruction to download an AI analysis model through the microphone 51, and when receiving a model download instruction through speech recognition, the control component 22 controls the network component 52 to download the AI analysis model. Alternatively, in a first-time use, or when the AI analysis model has an updated version, the control component 22 may directly download the target AI analysis model using the network component 52 without a model download instruction input by a user through a speech.

The control component 22 is further configured to upload the pathological report or the case history report to a first target device through the network component 52.

The control component 22 is further configured to upload, through the network component 52, an AI pathological image superimposed with the AI analysis information to a second target device or share, using the network component 52, an AI pathological image superimposed with the AI analysis information to a preset sharing channel.

In some embodiments, when the pathologic microscope 200 is used in a hospital, the first target device may include a hospital information system or a cloud server used inside the hospital, or when the pathologic microscope 200 is used in a scientific research laboratory, the first target device includes a laboratory information system or a cloud server used inside the laboratory. Furthermore, when the pathologic microscope 200 is used in a school, the first target device includes at least one of a school teaching information system or a cloud server used inside a school.

When the pathologic microscope 200 is used in the hospital, the second target device includes a pathological image database of the hospital information system, or when the pathologic microscope 200 is used in the scientific research laboratory, the second target device includes a pathological image database of the laboratory information system, or when the pathologic microscope 200 is used in the school teaching, the second target device includes a pathological image database of the school teaching information system.

The preset sharing channel may include at least one of an instant messaging platform, a medical communication platform, a journal of medical research, or a medical research forum.

In some embodiments, the pathologic microscope 200 further includes a speech playback component 53 connected to the control component 22.

In some embodiments, the control component 22 is further configured to send a pathological digital image to a server. The server may store an AI analysis model and configured to perform AI analysis on the pathological digital image by using the AI analysis model to obtain the AI analysis information. The control component 22 is further configured to receive the AI analysis information from the server. The server may be a single server, a server cluster including a plurality of servers, or a cloud server running on a cloud.

The control component 22 is further configured to control the speech playback component 53 to play the AI analysis information. For example, when obtaining AI analysis information of a pathological section by using the AI analysis model, the pathologic microscope 200 may play the AI analysis information by using the speech playback component 53.

That is, according to the pathologic microscope provided in this embodiment, an image acquisition component acquires a pathological digital image, and a control component performs AI analysis on the pathological digital image to obtain AI analysis information. The AR projection component projects the AI analysis information onto a microscopic field of a microscope body, so that a doctor can directly observe a pathological section image and the AI analysis information in the microscopic field at the same time, and does not need to switch a visual field back and forth in the entire observation process. This makes the observation process of the pathologic microscope simpler and more direct, thereby achieving a high real-time performance of the pathologic microscope in the observation process.

According to the pathologic microscope provided in this embodiment, the control component is further configured to obtain at least one AI analysis model. As factors such as the immersion reagent and the use scenario vary, the pathological section changes differently, and different analysis requirements are imposed in AI analysis. However, depending on the situation, a single AI analysis model may not be able to adjust a model parameter according to an actual use scenario and ensure accuracy and stability in actual use. As such, a plurality of different AI analysis models may be used to adapt to different actual use scenarios, thereby ensuring accuracy and stability of use.

According to the pathologic microscope provided in this embodiment, a speech acquisition component is connected to the control component. The speech acquisition component acquires an external speech signal and sends the speech signal to the control component. The control component forms a control instruction by recognizing the speech signal, and the pathologic microscope may be controlled according to the control instruction, in which an operation of physical button control may be omitted, thereby implementing a speech interaction operation of the pathologic microscope and improving man-machine interaction efficiency of a doctor. In a scenario such as diagnosis or surgery, a doctor can smoothly use the pathologic microscope.

Furthermore, in a case that the control instruction is a model selection instruction, a target AI analysis model is selected according to the model selection instruction. According to an actual use scenario, a user transmits a speech signal through a microphone, the control component recognizes the speech signal to form a control instruction, content of the control instruction is a model selection instruction, and a target AI analysis model corresponding to the actual use scenario is selected according to the model selection instruction.

In a case that the control instruction is a model download instruction, at least one AI analysis model is downloaded by using a network component or interface, or in a case that a target AI analysis model is not stored, the target AI analysis model is downloaded by using a network component. The AI analysis model is obtained or updated, thereby ensuring that the AI analysis model can be applicable to a use scenario and ensuring accuracy and stability of a result.

In addition, the control component may transmit a pathological digital image to a server, and an AI analysis model stored in the server may perform AI analysis on the pathological digital image. Thereafter, the control component may receive the AI analysis information from the server. Even if the control component does not store the AI analysis model, the control component may also obtain AI analysis information by communicating with the server that stores AI analysis models and performs analysis based on the stored AI models, thereby reducing load on the pathologic microscope end and ensuring that the AI analysis model can still be applicable to a variety of scenarios.

When the control instruction is to generate a report, the pathologic microscope automatically generates a pathological report or a case history report according to the AI analysis information, to integrate the pathological digital image and a doctor analysis result, thereby providing a basis for formulating a later treatment solution.

The control component further recognizes text content from the speech signal and generates a doctor record in the pathological report or the case history report according to the text content. Speech content recognized by the control component is expressed in a text form, and a doctor may perform professional diagnosis according to the AI analysis information, thereby avoiding complexity of typing on a keyboard.

The network component further uploads or shares at least one of a pathological image, a pathological digital image, and an AI pathological image, and a corresponding report, and induction-arrangement and storage of pathological information are implemented, thereby reducing a task volume of a user of memorizing a large quantity of images and reducing repetitive memory.

The control component further controls a speech playback component to play the AI analysis information, so that a process in which a doctor views paper information or electronic information may be avoided, and the doctor only needs to listen to the played information to perform professional diagnosis, thereby improving diagnosis efficiency.

In an embodiment based on FIG. 7, two different implementations of the pathologic microscope 200 are shown as examples.

Figure 10:
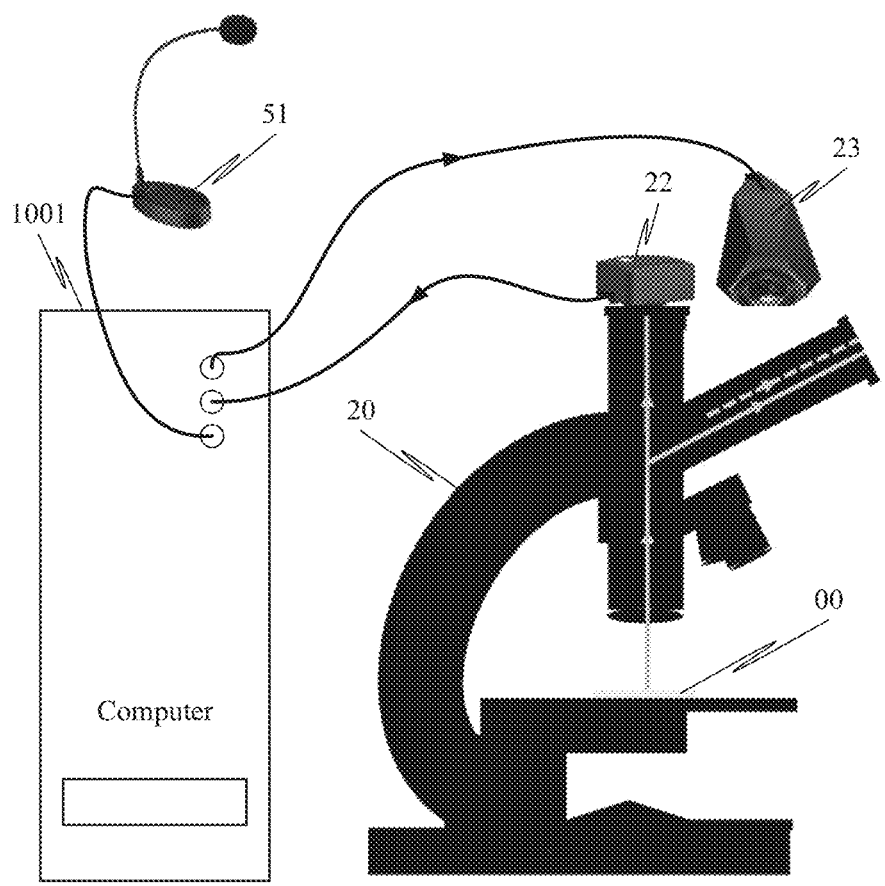
FIG. 10 is a first schematic structural diagram of a pathologic microscope according to an embodiment.

In an embodiment, the image acquisition component 21, the control component 22, and the network component 52 may be implemented by using an electronic device disposed outside the microscope body. As shown in FIG. 10, the microscope body of the pathologic microscope 200 includes a first body part corresponding to the incident optical path and a second body part corresponding to the outgoing optical path. A first physical interface is formed on the first body part, and the first physical interface may be a preset standard interface such as a threaded interface or a clip interface. The image acquisition component 21 may be a camera, a first physical connector is formed on the camera, and the first physical connector of the image acquisition component 21 is connected to the first physical interface on the first body part. Correspondingly, a second physical interface is formed on the second body part, and the second physical interface may be a preset standard interface such as a threaded interface or a clip interface. A second physical connector is formed on the AR projection component 23, and the second physical connector of the AR projection component 23 is connected to the second physical interface on the second body part. For example, the control component 22 and the network component 52 are further implemented by using a computer 1001, and a microphone is used as the speech acquisition component 51. The pathological section 00 is located on an object stage of the microscope body 20, the image acquisition component 21 is located on the incident optical path, and the image acquisition component 21 is electrically connected to an input end of the computer 1001. The AR projection component 23 is electrically connected to an output end of the computer 1001, and the AR projection component 23 is disposed on the outgoing optical path, and the outgoing optical path is located in an eyepiece tube of the microscope body 20.

Figure 11:
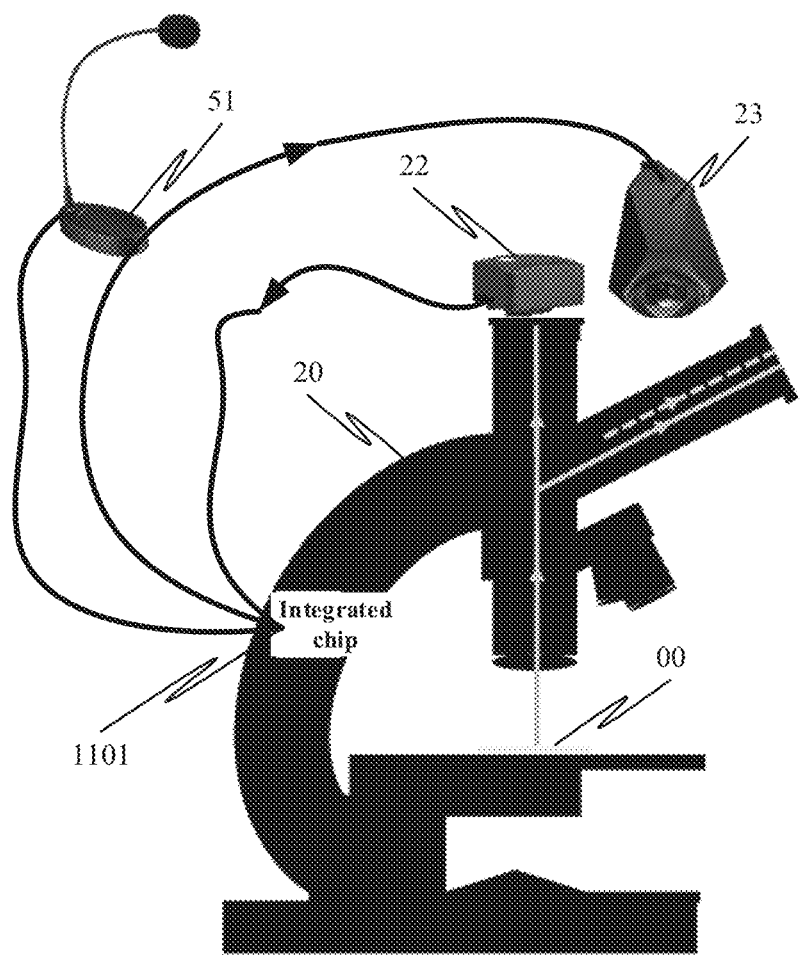
FIG. 11 is a second schematic structural diagram of a pathologic microscope according to an embodiment.

In an embodiment, the control component 22 (and at least one of the network component 52 or the speech playback component 53) may be manufactured into an integrated chip 1101. As shown in FIG. 11, the integrated chip 1101 is integrally formed at a microscope arm of the microscope body, and a microphone is used as the speech acquisition component 51. The pathological section 00 is located on the object stage of the microscope body 20, the image acquisition component 21 is located on the incident optical path, and the image acquisition component 21 is electrically connected to an input end of the integrated chip 1101. The AR projection component 23 is electrically connected to an output end of the integrated chip 1101, and the AR projection component 23 is disposed on the outgoing optical path, and the outgoing optical path is located in the eyepiece tube of the microscope body 20.

In some embodiments, a system of the pathologic microscope needs to save and/or upload, through a network, files such as a pathological image, a pathological report, and a case history report in the process of processing a pathological section image, and further needs to download and/or update the AI analysis model through the network. Therefore, the pathologic microscope may be provided with a wired network or a wireless network.

Figure 12:
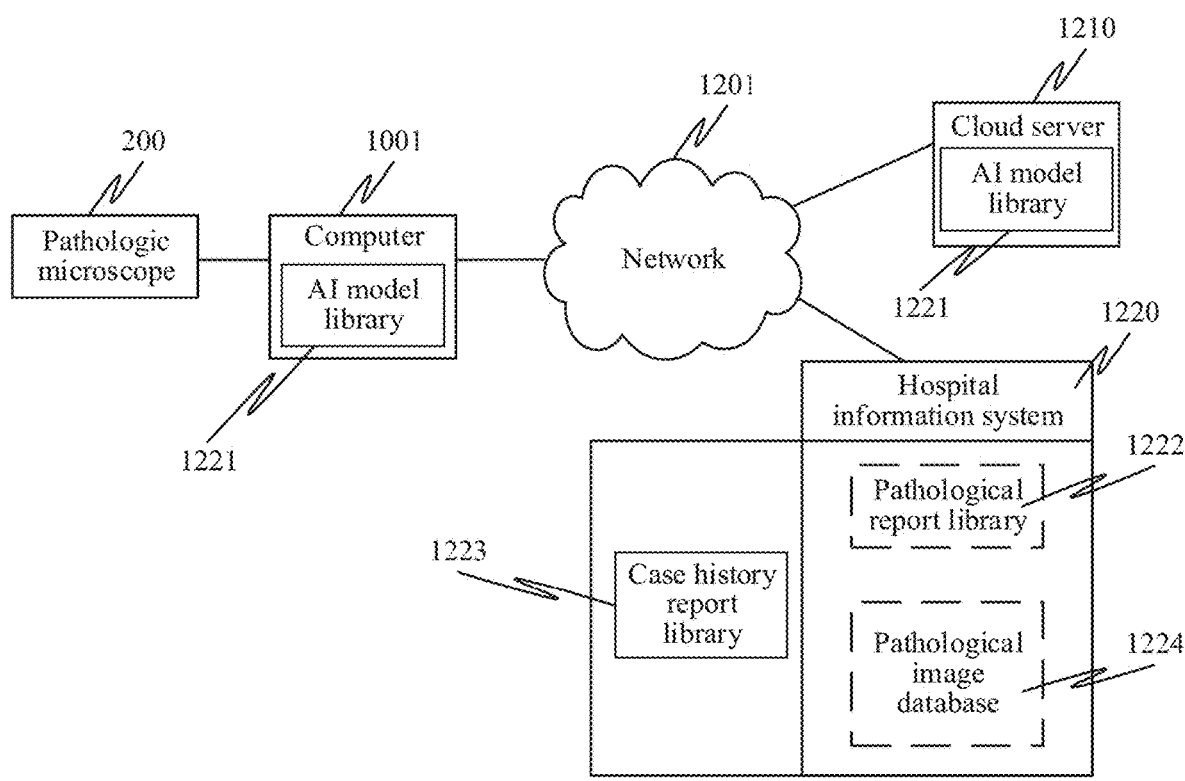
FIG. 12 is a diagram of an implementation environment of a pathologic microscope according to an embodiment.

FIG. 12 is a diagram of an implementation environment of a pathologic microscope according to an exemplary embodiment. The implementation environment includes a pathologic microscope 200, a network 1201, a cloud server 1210, and a hospital information system 1220.

The pathologic microscope 200 is manufactured by a manufacturer and provided to a doctor for use. The pathologic microscope 200 may be connected to the cloud server 1210 through a network, and may be connected to the hospital information system 1220 through the network.

The network 1201 may include a wired or a wireless network. When the pathologic microscope is connected to the hospital information system 1220 through the network 1201, based on privacy protection of a pathologic condition of a patient, the network may be a dedicated wired network inside a hospital. An isolation effect that other people cannot access except that the doctor uses the dedicated wired network through an internal computer of the hospital to use the pathologic microscope may be implemented.

The cloud server 1210 may be set up by a manufacturer of the pathologic microscope 200, and the manufacturer may publish an AI analysis model applicable to the pathologic microscope 200 and/or publish an updated version of the AI analysis model to the cloud server 1210. A purchaser or a user (for example, a hospital, a scientific institution, or a school) of the pathologic microscope 200 may download at least one of the AI analysis model or the updated version of the AI analysis model using the cloud server 1210. The download manner may be free or paid. The AI analysis model in the cloud server 1210 may be set up by technicians of the manufacturer.

The cloud server 1210 may be used as a storage location of the AI analysis model, that is, an AI model library 1221 is disposed inside the cloud server 1210, and the AI model library 1221 is configured to store the AI analysis model. After obtaining a pathological digital image, the pathologic microscope uploads the pathological digital image to the cloud server, the AI model library 1221 in the cloud server is invoked, and a target AI analysis model is selected according to a use scenario to perform AI analysis to obtain AI analysis information. Then, the AI analysis information is transmitted back to the pathologic microscope. The AI analysis model in the cloud server 1210 may be set up by the technicians of the manufacturer, or the AI analysis model may be uploaded to the cloud server 1210 by a developer.

The hospital information system 1220 includes a pathological report library 1222, a case history report library 1223, and a pathological image database 1224.

In a possible implementation, an AI model library 1221 is disposed inside a computer, and the AI model library 1221 may be configured to download at least one of the published AI analysis model or updated version of the AI analysis model from the cloud server 1210 for use by various departments in the hospital, so that the doctor does not need to separately download from the cloud server 1210. For example, if the doctor directly downloads the at least one of the AI analysis model or the updated version of the AI analysis model from the cloud server 1210, the doctor needs to register an account and pay a corresponding fee. However, after the hospital downloads the at least one of the AI analysis model or the updated version of the AI analysis model to the AI model library 1221, and when the doctor then downloads the AI analysis model and/or the updated version of the AI analysis model from the AI model library 1221, the doctor does not need to register an account additionally and does not need to pay a fee.

In another possible implementation, an AI model library 1221 may be disposed inside a computer, and the AI model library 1221 may be configured to publish an AI analysis model developed by a researcher of the hospital for the pathologic microscope 200. The AI analysis model developed by the hospital may include at least one of the following models an AI analysis model aiming at a pathological direction different from the AI analysis model provided by the manufacturer, an AI analysis model developed by the hospital superior to the AI analysis model provided by the manufacturer in some use scenarios, and an AI analysis model developed by the hospital that is not provided by the manufacturer.

In another possible implementation, if the pathologic microscope 200 does not locally store an AI analysis model, the AI model library 1221 disposed inside the computer may be configured to store the AI analysis model of the pathologic microscope 200. When the pathologic microscope 200 is in use, a corresponding AI analysis model in the computer needs to be invoked for AI analysis, and the doctor may log in to an account of the hospital information system 1220 before using the pathologic microscope 200. In this case, the doctor invokes the corresponding AI analysis model directly from the AI model library 1221 through the pathologic microscope 200.

However, the implementation of the AI model library 1221 is not limited to the above-described embodiments, but may include one or a combination of the above described types or any other implementation.

According to an embodiment, the pathologic microscope 200 includes a computer 1001, and the computer 1001 including the control component and the network component. After processing a pathological section image, the computer 1001 uploads the pathological section image and/or a pathological digital image and/or an AI pathological image to the pathological image database 1224 of the hospital information system 1220 through the network 1201, to implement sharing of related information of the pathological section image and/or the pathological digital image and/or the AI pathological image and expand richness of the pathological image database 1224 inside the hospital.

The pathologic microscope 200 generates a pathological report according to an operation of a user, for example, a pathological report according to a speech instruction and oral content of a doctor, and uploads the pathological report to the pathological report library 1222 of the hospital information system 1220 through the network 1201 to expand the pathological report library 1222 inside the hospital and store the pathological report electronically. The pathologic microscope 200 generates a case history report according to an operation of a user, for example, a case history report according to a speech instruction and oral content of a doctor, and uploads the case history report to the case history report library 1223 of the hospital information system 1220 through the network 1201 to expand the case history report library 1223 inside the hospital and store the case history report electronically.

The pathological image database 1224, the pathological report library 1222, and the case history report library 1223 are all electronic storage of at least one of the pathological image, the pathological digital image, or the AI pathological image information. The electronic storage may be used for subsequent statistical analysis and query, thereby expanding richness of the database. In an example, the electronic storage may be used for providing a learning case for a houseman to learn, and performing targeted diagnosis on the treatment condition of a particular patient in the past.

In this embodiment, the pathologic microscope 200 may be applied to a hospital application place, or may be applied to an application place such as a research institution or a school. However, the implementation environment is not limited thereto.

Figure 13:
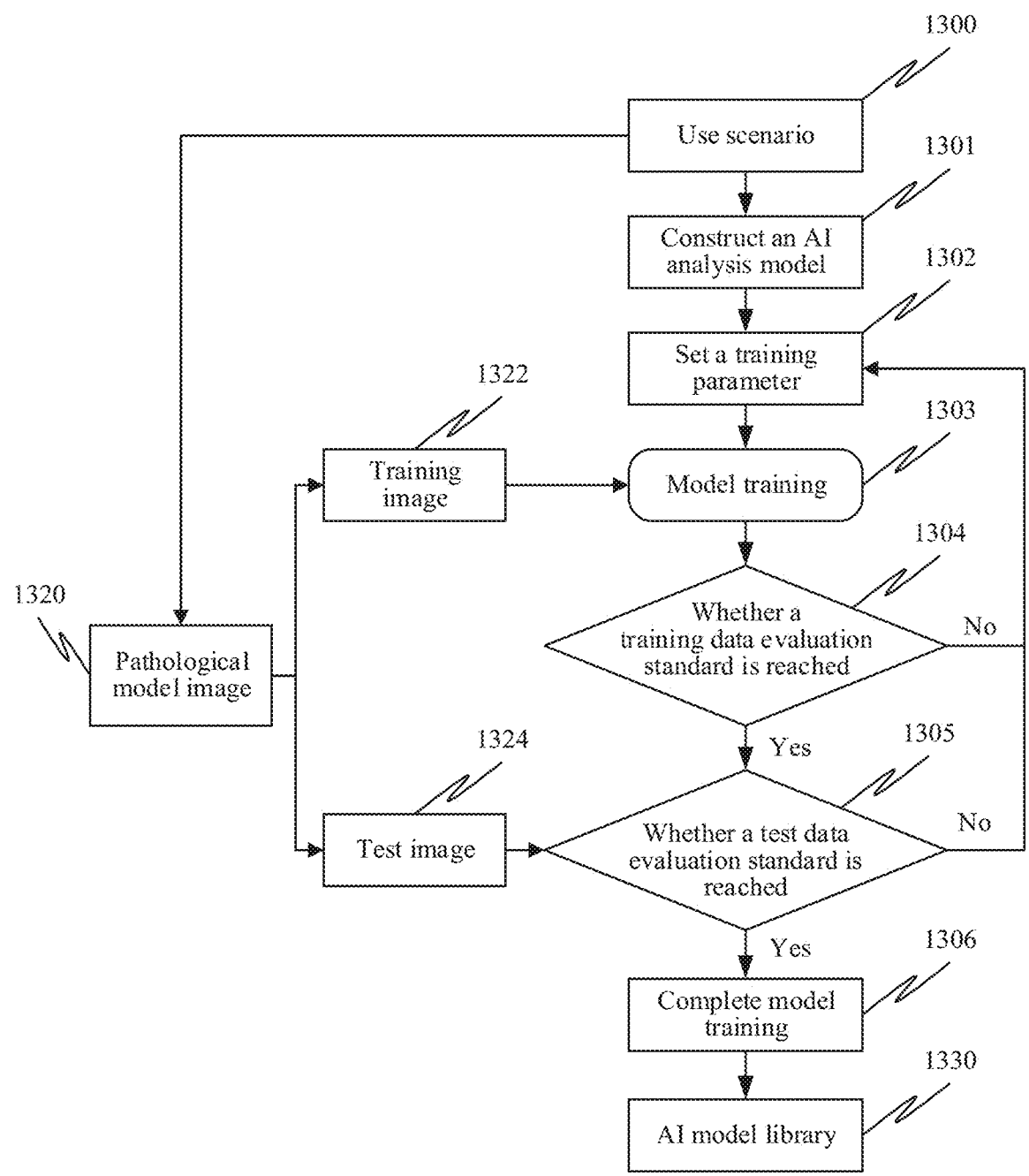
FIG. 13 is a flowchart of an AI analysis model training method of a pathologic microscope according to an embodiment.

In an embodiment based on FIG. 12, the AI analysis model may be trained by a technician of a hospital, or may be trained by a technician of a manufacturer of a pathologic microscope. For example, the training process is shown in FIG. 13.

Step 1300. Use scenario.

Here, a technician determines a use scenario of an AI analysis model. Typically, the AI analysis model may be an AI model for tumor analysis, an AI model for cell detection analysis, or an AI model for infectious disease detection analysis. However, the user scenario is not limited thereto, and may include any other scenarios in which the pathologic microscope may be utilized.

The technician determines a pathological model image 1320 required for model training, and the pathological model image 1320 may be a sample image library. One use scenario may correspond to one group of pathological model images, and different use scenarios may correspond to different groups of pathological model images. Each pathological model image is manually or machine labeled with a corresponding calibration result, and the calibration result is used for indicating an actual analysis result generated manually or by other machines.

The model training may be divided into a training process and a test process. For example, the same group of pathological model images (m) may include m=2000. Here, 2000 pathological model images may be further divided into m1=1800 training images 1322 and m2=200 test images 1324. The m1 training images 1322 are used for training the AI analysis model during training, and the m2 test images 1324 are used for performing a performance test on the trained AI analysis model during test.

In some embodiments, the m1 training images 1322 may be referred to as a training image set, and the m2 test images 1324 may be referred to as a test image set.

Step 1301. Construct an AI analysis model.

The technician further constructs corresponding AI analysis models for different use scenarios. The AI analysis model is a neural network model for processing an image, and the neural network model may be a deep neural network (DNN), a convolutional neural network (CNN), a recurrent neural network (RNN), or the like. However, the AI analysis model is not limited thereto.

A network type, a quantity of network layers, a composition form of neurons of each layer of network, a type of a neuron adopted by each layer of network, and a connection relationship between adjacent network layers of the AI analysis model may be set according to different use scenarios. That is, different AI analysis models may have the same network type or different network types, the same quantity of network layers or different quantities of network layers, the same composition form of neurons of each layer of network or different composition forms of neurons of each layer of network, the same type of a neuron adopted by each layer of network or different types of neurons adopted by each layer of network, or the same connection relationship between adjacent network layers or different connection relationships between adjacent network layers. However, the embodiment is not limited thereto.

Step 1302. Set a training parameter.

For one AI analysis model, each layer of neurons in the AI analysis model has a respective neuron parameter (or weight). Here, an initial parameter of each layer of neurons may be generated in a random manner, or an initial parameter of each layer of neurons in accordance with an empirical value.

The initial parameter is a neuron parameter of a neuron in the AI analysis model before training.

Step 1303. Model training.

Each training image 1322 in the training image set is sequentially inputted into an AI analysis model for training. The AI analysis model performs AI analysis on the training image 1322 to obtain a prediction result. The prediction result is compared with a calibration result of the training image 1322 to obtain an analysis error, and then a back propagation is performed on the analysis error according to an error back propagation algorithm to update a parameter of each layer of neurons of the AI analysis model.

Step 1304. Determine whether a training data evaluation standard is reached.

A training data evaluation standard (also referred to as a training finishing condition) may be set by a user or a technician. In an implementation, the training data evaluation standard is used so that a prediction error converges to an expected threshold. In another implementation, the training data evaluation standard is used so that a quantity of times of training iteration reaches a times threshold (for example, 10000).

After the neuron parameter is updated in each training process, the model may determine whether the training data evaluation standard is reached. When the training data evaluation standard is reached, step 1305 is performed, and when the training data evaluation standard is not reached, step 1303 is performed again.

For example, the a predetermined training finishing condition may be performing training iteration for 20,000 times, and when the number of training iteration reaches 20,000, the step 1305 may be performed. Otherwise, the iteration training process continues until it reaches 20,000.

Step 1305. Determine whether a test data evaluation standard is reached.

When the training process reaches the predetermined training finishing condition, each test image 1324 in the test image set may be inputted into the trained AI analysis model for testing. The evaluation data may include at least one test image in the test image set.

The test data evaluation standard may be that an error between a test result and a calibration result of the test image is less than a preset condition, accuracy of a test result of the test image is greater than a preset threshold, or both a test speed and a test result of the test image reach an expected condition. The test data evaluation standard may be different according to different actual use scenarios. However, this is not limited to this embodiment.

When the trained AI analysis model does not reach the test data evaluation standard, the trained AI analysis model is retrained. When the trained AI analysis model reaches the test data evaluation standard, step 1306 is performed.

Step 1306. Complete model training.

When the trained AI analysis model is determined as an AI analysis model that can be used, it may be stored in an AI model library 1330. The AI model library may be a library or a storage in the control component of the pathologic microscope, a database in a health care system of a hospital, or a cloud server.

In some embodiments, the pathologic microscope implements functions such as AI analysis and projection on a pathological image by controlling other components by the control component.

Figure 14:
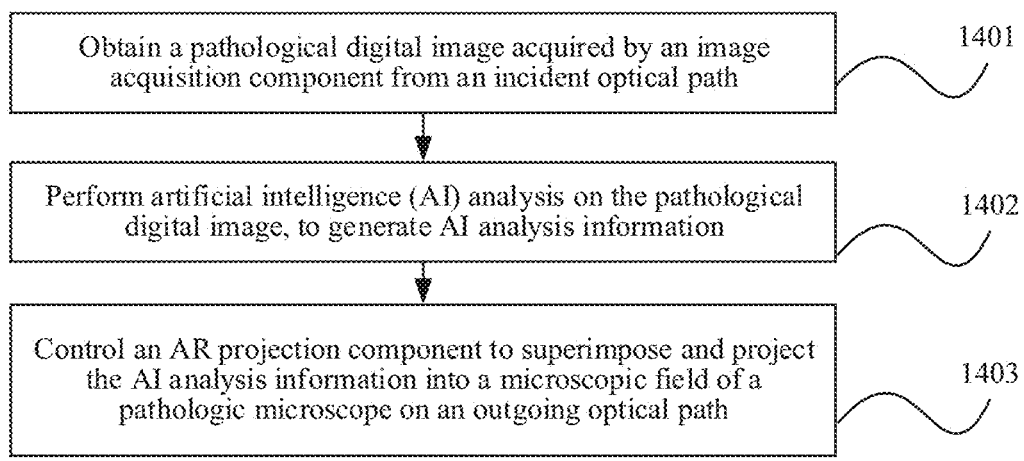
FIG. 14 is a flowchart of a display control method according to an embodiment.

FIG. 14 is a flowchart of a display control method according to an exemplary embodiment. The method may be applied to the control component of the pathologic microscope provided by the embodiments, and the method includes the following steps:

Step 1401. Obtain a pathological digital image acquired by an image acquisition component from an incident optical path.

The image acquisition component is located on the incident optical path of a microscope body, acquires a pathological image of a pathological section on an object stage, and performs image preprocessing on the pathological image inside the image acquisition component to obtain the pathological digital image.

Step 1402. Perform AI analysis on the pathological digital image to generate AI analysis information.

The AI analysis information is information obtained by analyzing the pathological digital image by using an AI analysis model.

There are two manners of obtaining the AI analysis model and performing AI analysis on the pathological digital image by using the pathologic microscope, and a specific implementation may be any one of the following:

First manner: The AI analysis model is disposed inside the control component and is configured to perform the AI analysis on the pathological digital image. In a possible embodiment, at least one AI analysis model is obtained, and a target AI analysis model corresponding to a use scenario of the pathological digital image is determined. The target AI analysis model may be invoked to perform the AI analysis on the pathological digital image to generate the AI analysis information.

Second manner: The AI analysis model is disposed inside a server and is configured to perform the AI analysis on the pathological digital image. In a possible embodiment, the control component sends the pathological digital image to a server. The server storing an AI analysis model may be configured to perform the AI analysis on the pathological digital image by using the AI analysis model to obtain the AI analysis information. The server then sends the AI analysis information to the control component. The control component receives the AI analysis information from the server and provide the AI analysis information for a user.

In some embodiments, when the server sends the AI analysis information to the control component, it may be that after the control component sends a download request to the server, the server sends the AI analysis information to the control component according to the download request, or the server directly sends the AI analysis information to the control component after analyzing to obtain the AI analysis information.

The process in which the server obtains the AI analysis information through the AI analysis may be similar to the process in which the control component obtains the AI analysis information through the AI analysis in the first manner.

In some embodiments, the server may be a single server, a server cluster including a plurality of servers, or a cloud server. In some embodiments, the server may be implemented as a cloud server shown in FIG. 12.

Step 1403. Control an AR projection component to project the AI analysis information into a microscopic field of a pathologic microscope on an outgoing optical path.

In some embodiments, the AI analysis information includes at least one of a text, a curve, a background color, or an animation. After the AI analysis information is superimposed with an image (or a picture) in the microscopic field, an AI pathological image (or an AI pathological picture) can be formed.

In some embodiments, the microscope body includes a first body part corresponding to the incident optical path and a second body part corresponding to the outgoing optical path. In an embodiment, the image acquisition component is integrated into the first body part and the AR projection component is integrated into the second body part. In another embodiment, a first physical interface is formed on the first body part, a first physical connector is formed on the image acquisition component, and the first physical connector of the image acquisition component is connected to the first physical interface of the first body part. Correspondingly, a second physical interface is formed on the second body part, a second physical connector is formed on the AR projection component, and the second physical connector of the AR projection component is connected to the second physical interface of the second body part. For example, the first physical interface and the second physical interface are at least one of a threaded interface, a socket, or a clamp interface.

According to an embodiment, an image acquisition component acquires a pathological digital image, a control component performs AI analysis on the pathological digital image to obtain AI analysis information, and an AR projection component projects the AI analysis information into a microscopic field of a microscope body, so that a doctor can directly observe a pathological section image and the AI analysis information in the microscopic field at the same time. Therefore, it reduces the burden of a user having to switch a visual field back and forth in the entire observation process, and makes the observation process of the pathologic microscope simpler and more direct, thereby achieving a high real-time performance of the pathologic microscope in the use process.

In some embodiments, in addition to implementing the AI analysis and projection on the pathological image, the control component is further configured to implement at least one of the functions such as generation of a pathological report and a case history report, download of the AI analysis model, and upload of the pathological image, the pathological report, or the case history report. Therefore, the control component has a control method to achieve a control purpose.

Figure 15:
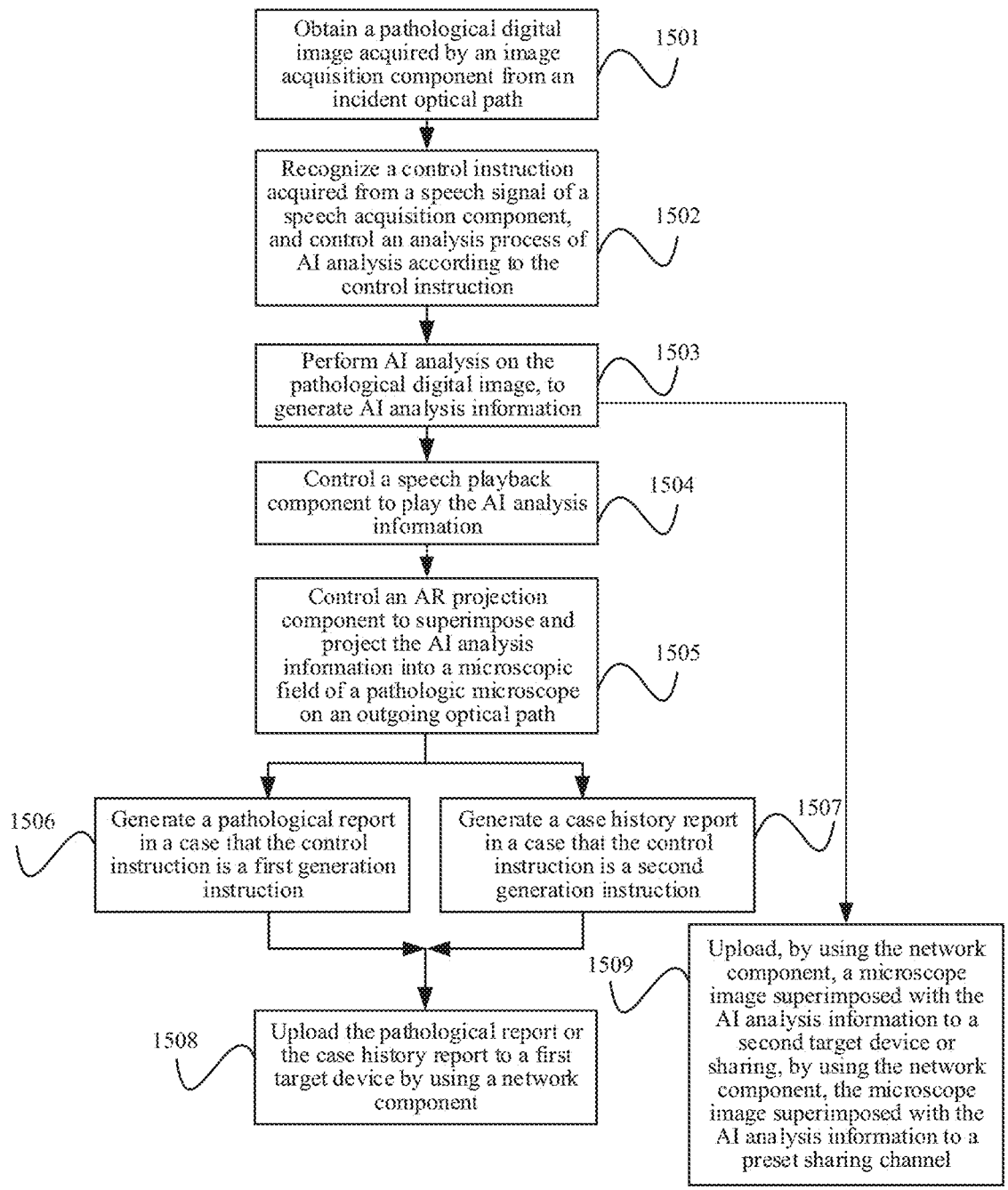
FIG. 15 is a method flowchart of a display control method according to an embodiment.

FIG. 15 is a flowchart of a display control method according to an embodiment. The method may be applied to the control component of the pathologic microscope, and the method includes the following steps:

Step 1501. Obtain a pathological digital image acquired by an image acquisition component from an incident optical path.

Step 1502. Recognize a control instruction acquired from a speech signal of a speech acquisition component, and control an analysis process of AI analysis according to the control instruction.

A microphone may be used as the speech acquisition component to acquire an external speech signal and send the speech signal to the control component. The control component recognizes content of the speech signal, and when the recognized content conforms to a preset control keyword, a corresponding control instruction is generated and the control component performs a corresponding control operation on the pathologic microscope according to the control instruction. In some embodiments, a speech recognition engine is disposed in the control component, and the speech signal is recognized by using the speech recognition engine.

In a case that the control instruction is a model selection instruction, a target AI analysis model is selected according to the model selection instruction. For example, the target AI analysis model includes a tumor area detection AI model, a cell detection AI model, and in infectious disease detection AI model. According to an actual use scenario, a user inputs a speech signal to the control component by using the microphone, and the control component recognizes the speech signal to obtain a control instruction. In a case that the control instruction is a model selection instruction, the control component selects, according to the model selection instruction, a target AI analysis model corresponding to the actual use scenario.

When a user issues a control command through the microphone, the control component forms a control instruction, and the control instruction can control a network component.

In a case that the control instruction is a model download instruction, the control component downloads at least one AI analysis model using the network component, or in a case that the target AI analysis model is not stored, the control component automatically downloads the target AI analysis model by using the network component.

Step 1503. Perform AI analysis on the pathological digital image to generate AI analysis information.

For a description of step 1503, reference may be made to step 1402.

Step 1504. Control a speech playback component to play the AI analysis information.

For example, when obtaining AI analysis information of a pathological section by using an AI analysis model, the pathologic microscope may play the AI analysis information by using the speech playback component.

Step 1505. Control an AR projection component to project the AI analysis information into a microscopic field of a pathologic microscope on an outgoing optical path.

Step 1506. Generate a pathological report in a case that the control instruction is a first generation instruction.

The pathological report includes AI analysis information. The pathological report is a report formed after a doctor inputs oral content through the microphone 51 according to the AI analysis information. For example, the AI analysis information includes appearance information of a pathological tissue and lesion information of a pathological cell, and the oral content includes pathological diagnosis of a doctor.

Step 1507. Generate a case history report in a case that the control instruction is a second generation instruction.

The case history report includes the AI analysis information and patient information, and the patient information is recognized from a text or a graphic code on a pathological section, or may be inputted by the doctor by using the speech acquisition component. In some embodiments, text content is recognized from a speech signal and a doctor record in the pathological report or the case history report is generated according to the text content. The control component recognizes a speech signal, and expresses content of the speech signal in a text form to form text content corresponding to the speech signal.

Step 1508. Upload the pathological report or the case history report to a first target device using a network component.

In some embodiments, when the pathologic microscope is used in a hospital, the first target device includes a hospital information system or a cloud server used inside the hospital, or when the pathologic microscope is used in a scientific research laboratory, the first target device includes a laboratory information system or a cloud server used inside a laboratory, or when the pathologic microscope is used in school, the first target device includes a school teaching information system or a cloud serve used inside a school.

Step 1509. Upload, through the network component, a microscope image superimposed with the AI analysis information to a second target device, or sharing, through the network component, the microscope image superimposed with the AI analysis information to a preset sharing channel.

In some embodiments, when the pathologic microscope is used in the hospital, the second target device includes a pathological image database of the hospital information system. When the pathologic microscope is used in the scientific research laboratory, the second target device includes a pathological image database of the laboratory information system, or when the pathologic microscope is used in the school, the second target device includes a pathological image database of the school teaching information system.

The preset sharing channel includes at least one of an instant messaging platform, a medical communication platform, a journal of medical research, or a medical research forum.

The steps in this embodiment are merely used for describing content of the display control method, and in an actual use process, a sequential order of the steps is not specifically limited.

According to an embodiment, an image acquisition component acquires a pathological digital image, a control component performs AI analysis on the pathological digital image to obtain AI analysis information, and an AR projection component projects the AI analysis information into a microscopic field of a microscope body, so that a doctor can directly observe a pathological section image and the AI analysis information in the microscopic field at the same time. Therefore, it reduces the burden of a user having to switch a visual field back and forth in the entire observation process to make the observation process of the pathologic microscope simpler and more direct, thereby achieving a high real-time performance of the pathologic microscope in the use process.

In addition, the control component may be further configured to obtain at least one AI analysis model. As factors such as the immersion reagent and the use scenario vary, the pathological section changes, and different analysis requirements may be imposed on the AI analysis. However, a single AI analysis model cannot adjust a model parameter according to an actual use scenario and cannot ensure accuracy and stability in actual use. A plurality of different AI analysis models can adapt to different actual use scenarios, thereby ensuring accuracy and stability of use.

Furthermore, a speech acquisition component is connected to the control component. The speech acquisition component acquires an external speech signal and sends the speech signal to the control component, the control component forms a control instruction after recognizing the speech signal, the control instruction controls the pathologic microscope, and an operation of button control is omitted, thereby implementing a speech interaction operation of the pathologic microscope and improving man-machine interaction efficiency of a doctor. In a scenario such as diagnosis or surgery, a doctor can smoothly use the pathologic microscope.

In a case that the control instruction is a model selection instruction, a target AI analysis model is selected according to the model selection instruction. According to an actual use scenario, when a user speaks or transmits a speech signal through a microphone, the control component recognizes the speech signal and generates a corresponding control instruction. When the content of the control instruction is a model selection instruction, and a target AI analysis model corresponding to the actual use scenario is selected according to the model selection instruction.

Furthermore, in a case that the control instruction is a model download instruction, at least one AI analysis model is downloaded through a network component, or in a case that a target AI analysis model is not stored, the target AI analysis model is downloaded using a network component. The AI analysis model is obtained or updated, thereby ensuring that the AI analysis model can be applicable to a use scenario and ensuring accuracy and stability of a result.

According to an embodiment, the control component sends a pathological digital image to a server, an AI analysis model stored in the server performs AI analysis on the pathological digital image, and the control component receives obtained AI analysis information. Even if the control component does not store the AI analysis model, the control component may also obtain AI analysis information by using the server, thereby ensuring that the AI analysis model can be applicable to a use scenario and ensuring accuracy and stability of a result.

According to an embodiment, when the control instruction is to generate a report, the pathologic microscope automatically generates a pathological report or a case history report according to the AI analysis information, to integrate the pathological digital image and a doctor analysis result, thereby providing a basis for formulating a later treatment solution.

According to an embodiment, the control component recognizes content from the speech signal and generates a doctor record in the pathological report or the case history report according to the content. Speech content recognized by the control component is expressed in a text form, and a doctor may perform professional diagnosis according to the AI analysis information, thereby avoiding complexity of typing on a keyboard.

According to an embodiment, a network component uploads or shares at least one of a pathological image, a pathological digital image, or an AI pathological image, and a corresponding report, and induction-arrangement and storage of pathological information are implemented, thereby reducing a task volume of a user of memorizing a large quantity of images and reducing repetitive memory.

According to an embodiment, the control component controls a speech playback component to play the AI analysis information, so that a process in which a doctor views paper information or electronic information may be avoided, and the doctor only needs to listen to the played information to perform professional diagnosis, thereby improving diagnosis efficiency.

Figure 16:
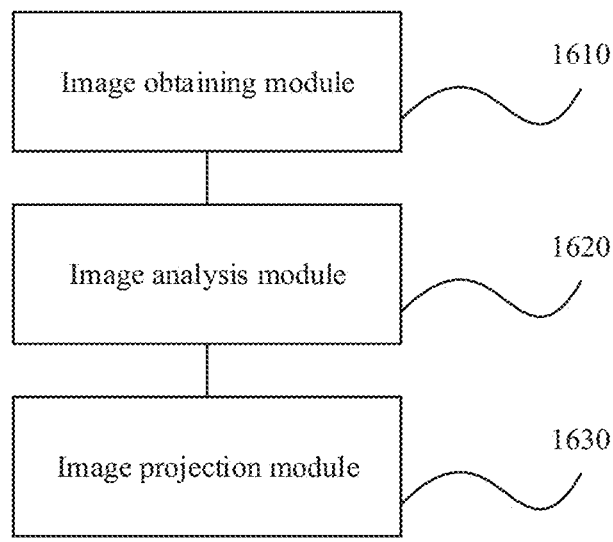
FIG. 16 is a block diagram of a display control apparatus according to an embodiment.
Figure 17:
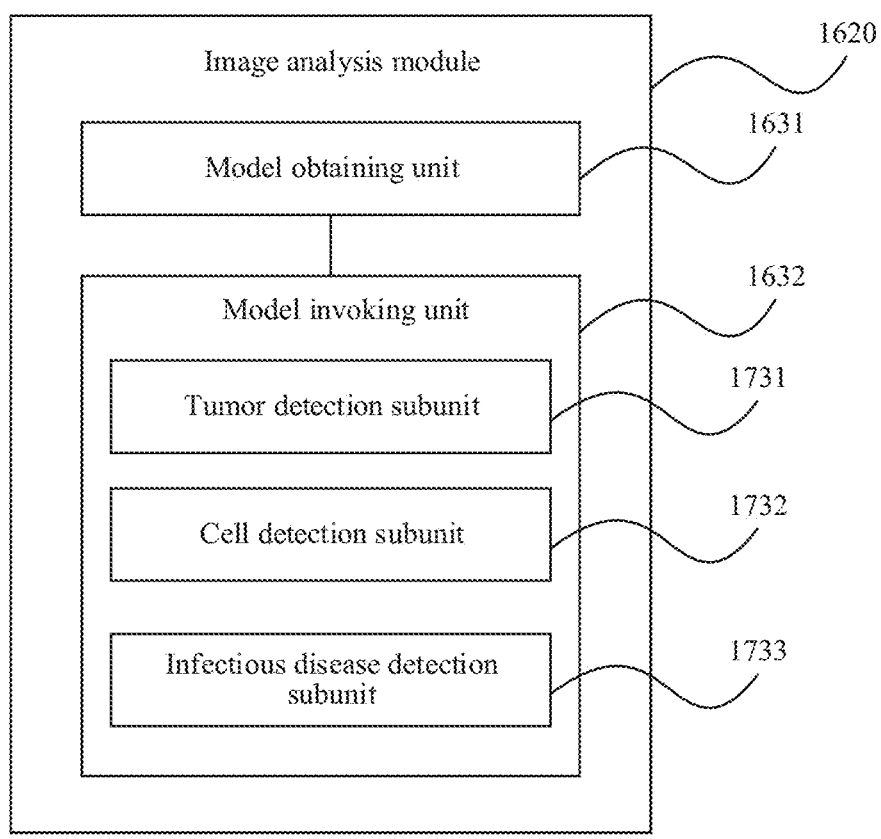
FIG. 17 is a block diagram of an image analysis module according to an embodiment.

FIG. 16 is a schematic diagram of a display control apparatus according to an exemplary embodiment. The apparatus may be configured in the control component of the pathologic microscope provided in the method embodiments, and the apparatus includes an image obtaining module 1610 configured to obtain a pathological digital image acquired by an image acquisition component from an incident optical path; and an image analysis module 1620 configured to perform AI analysis on the pathological digital image to generate AI analysis information. As shown in FIG. 17, the image analysis module 1620 may include a model obtaining unit 1631 and a model invoking unit 1632. The model obtaining unit 1631 is configured to obtain at least one AI analysis model and determine a target AI analysis model corresponding to a use scenario of the pathological digital image. The model invoking unit 1632 is configured to invoke the target AI analysis model to perform the AI analysis on the pathological digital image to generate the AI analysis information.

Different AI analysis models have different analysis capabilities, and one or more AI analysis models may be disposed inside the model invoking unit 1632. At least one of a tumor area detection AI model, a cell detection AI model, or an infectious disease detection AI model may be disposed in the model invoking unit 1632.

For example, the tumor area detection AI model, the cell detection AI model, and the infectious disease detection AI model are simultaneously disposed in the model invoking unit 1632. As shown in FIG. 17, the model invoking unit 1632 includes a tumor detection subunit 1731, a cell detection subunit 1732, and an infectious disease detection subunit 1733. However, the embodiment is not limited thereto, and the model invoking unit 1632 may include other subunits according to the needs of the AI model.

The tumor detection subunit 1731 is further configured to determine the tumor area detection AI model as a target AI analysis model in a case that a use scenario of the pathological digital image is tumor area detection, and invoke the tumor area detection AI model to perform the AI analysis on the pathological digital image to obtain tumor analysis information. The cell detection subunit 1732 is further configured to determine the cell detection AI model as a target AI analysis model in a case that a use scenario of the pathological digital image is cell detection, and invoke the cell detection AI model to perform the AI analysis on the pathological digital image to obtain cell detection information.

The infectious disease detection subunit 1733 is further configured to determine the infectious disease detection AI model as a target AI analysis model in a case that a use scenario of the pathological digital image is infectious disease detection, and invoke the infectious disease detection AI model to perform the AI analysis on the pathological digital image to obtain infectious disease detection information. In some embodiments, the control component further downloads an AI analysis model from other devices on a local area network or a wide area network. For example, the control component downloads the AI analysis model from the other devices according to a current use scenario.

Furthermore, the image analysis module may include an image sending unit and an information receiving unit. The image sending unit is configured to send the pathological digital image to a server, the server storing an AI analysis model and being configured to perform the AI analysis on the pathological digital image by using the AI analysis model, to obtain the AI analysis information.

The information receiving unit is configured to receive the AI analysis information sent by the server. An image projection module 1630 is configured to control an AR projection component to project the AI analysis information into a microscopic field of a pathologic microscope on an outgoing optical path.

Therefore, an image acquisition component acquires a pathological digital image, a control component performs AI analysis on the pathological digital image to obtain AI analysis information, and an AR projection component projects the AI analysis information into a microscopic field of a microscope body. This allows a doctor or a user to directly observe a pathological section image and the AI analysis information in the microscopic field at the same time, and does not need to switch a visual field back and forth in the entire observation process to make the observation process of the pathologic microscope simpler and more direct, thereby achieving a high real-time performance of the pathologic microscope in the use process and providing convenience to the user.

Figure 18:
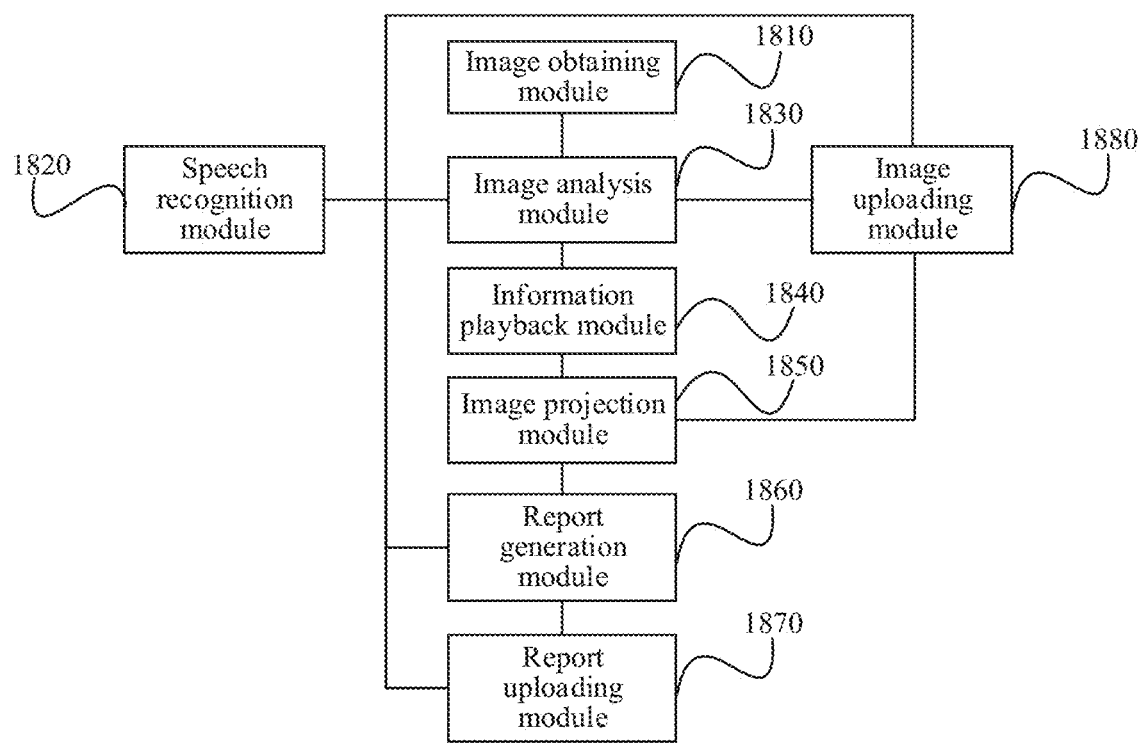
FIG. 18 is a block diagram of a display control apparatus according to an embodiment.

FIG. 18 is a schematic diagram of a display control apparatus according to an exemplary embodiment. The apparatus may be configured in the control component of the pathologic microscope provided in the method embodiments. The apparatus includes an image obtaining module 1810 configured to obtain a pathological digital image acquired by an image acquisition component from an incident optical path; a speech recognition module 1820, configured to recognize a control instruction acquired from a speech signal of a speech acquisition component, and control an analysis process of AI analysis according to the control instruction; and an image analysis module 1830, configured to perform AI analysis on the pathological digital image to generate AI analysis information.

The AI analysis information is result information obtained by analyzing the pathological digital image by using an AI analysis model. In an embodiment, an AI analysis model is disposed inside the apparatus and is configured to perform the AI analysis on the pathological digital image. Here, at least one AI analysis model is obtained, a target AI analysis model corresponding to a use scenario of the pathological digital image is determined, and the target AI analysis model is invoked to perform the AI analysis on the pathological digital image to generate the AI analysis information.

Different AI analysis models have different analysis capabilities, and one or more AI analysis models may be disposed inside the apparatus. At least one of a tumor area detection AI model, a cell detection AI model, or an infectious disease detection AI model is simultaneously disposed in the apparatus.

The image analysis module includes an image sending unit and an information receiving unit. The image sending unit is configured to send the pathological digital image to a server, the server storing an AI analysis model and being configured to perform the AI analysis on the pathological digital image by using the AI analysis model, to obtain the AI analysis information.

The information receiving unit is configured to receive the AI analysis information sent by the server.

An information playback module 1840 is configured to control a speech playback component to play the AI analysis information.

An image projection module 1850 is configured to control an AR projection component to project the AI analysis information into a microscopic field of a pathologic microscope on an outgoing optical path.

A report generation module 1860 is configured to generate a pathological report in a case that the control instruction is a first generation instruction, the pathological report including the AI analysis information.

In addition, a report generation module is configured to generate a case history report in a case that the control instruction is a second generation instruction, the case history report including the AI analysis information and patient information, and the patient information being recognized from a text or a graphic code on a pathological section, or being inputted by the doctor by using the speech acquisition component.

In some embodiments, audio content is recognized from a speech signal and converted into text so that a doctor record in the pathological report or the case history report is generated in the text content. The apparatus recognizes a speech signal, and expresses content of the speech signal in a text form corresponding to the speech signal.

A report uploading module 1870 is configured to upload the pathological report or the case history report to a first target device by using a network component.

An image uploading module 1880 is configured to upload, by using the network component, a microscope image superimposed with the AI analysis information to a second target device or sharing, by using the network component, the microscope image superimposed with the AI analysis information to a preset sharing channel.

Figure 19:
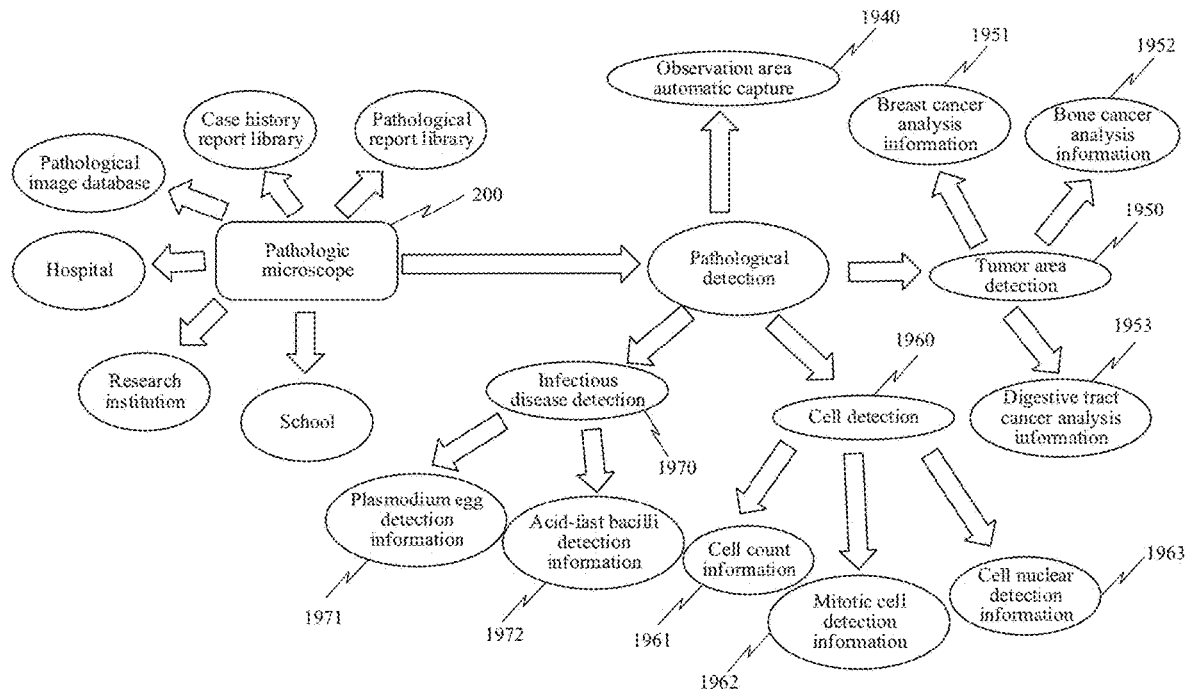
FIG. 19 is a schematic diagram of an applicable place of a pathologic microscope according to an embodiment.

A use scenario of the pathologic microscope 200 is used as an example for description. As shown in FIG. 19, the pathologic microscope 200 may be used in various places such as a hospital, a research institution, and a school, and a pathological image database, a case history report library, and a pathological report library may exist in the hospital, the research institution, and the school, that is, a hospital information system exists in the hospital and the hospital information system includes the pathological image database, the case history report library, and the pathological report library; a research institution information system exists in the research institution and the research institution information system includes the pathological image database, the case history report library, and the pathological report library; and a school information system exists in the school and the school information system includes the pathological image database, the case history report library, and the pathological report library.

The pathological image database is a database for storing at least one of an uploaded pathological section image, an uploaded pathological digital image, or an uploaded AI pathological image, and archives a pathological section analyzed by the pathologic microscope 200. The pathological report library is a database for storing an uploaded pathological report, includes AI analysis information, and classifies and stores pathological section information detected at a use place. The case history report library is a database for storing an uploaded case history report, the case history report includes AI analysis information and patient information, and the patient information is recognized from a text or a graphic code on a pathological section. The case history report library can invoke the patient information, where a report result corresponds to the patient information, classifies and stores the patient information and the case history report, and tracks a revisit record of a patient.

When performing pathological detection, the pathologic microscope 200 can capture an observation area automatic capture 1940, for example, the observation area automatic capture 1940 is a suspicious lesion area. Then, a target AI analysis model is selected according to a use scenario to perform AI analysis.

The tumor area detection AI model is determined as the target AI analysis model in a case that the use scenario is tumor area detection 1950, and the tumor area detection AI model is invoked to perform the AI analysis on a pathological digital image to obtain tumor analysis information. The tumor analysis information includes any one of breast cancer analysis information 1951, bone cancer analysis information 1952, and digestive tract cancer analysis information 1953.

The cell detection AI model is determined as the target AI analysis model in a case that the use scenario of the pathological digital image is cell detection 1960, and the cell detection AI model is invoked to perform the AI analysis on the pathological digital image to obtain cell detection information. In some embodiments, the cell detection information includes any one of cell count information 1961, mitotic cell detection information 1962, and cell nuclear detection information 1963.

The infectious disease detection AI model is determined as the target AI analysis model in a case that the use scenario of the pathological digital image is infectious disease detection 1970. The infectious disease detection AI model is invoked to perform the AI analysis on the pathological digital image to obtain infectious disease detection information. The infectious disease detection information includes any one of plasmodium egg detection information 1971 and acid-fast bacilli detection information 1972.

Figure 20:
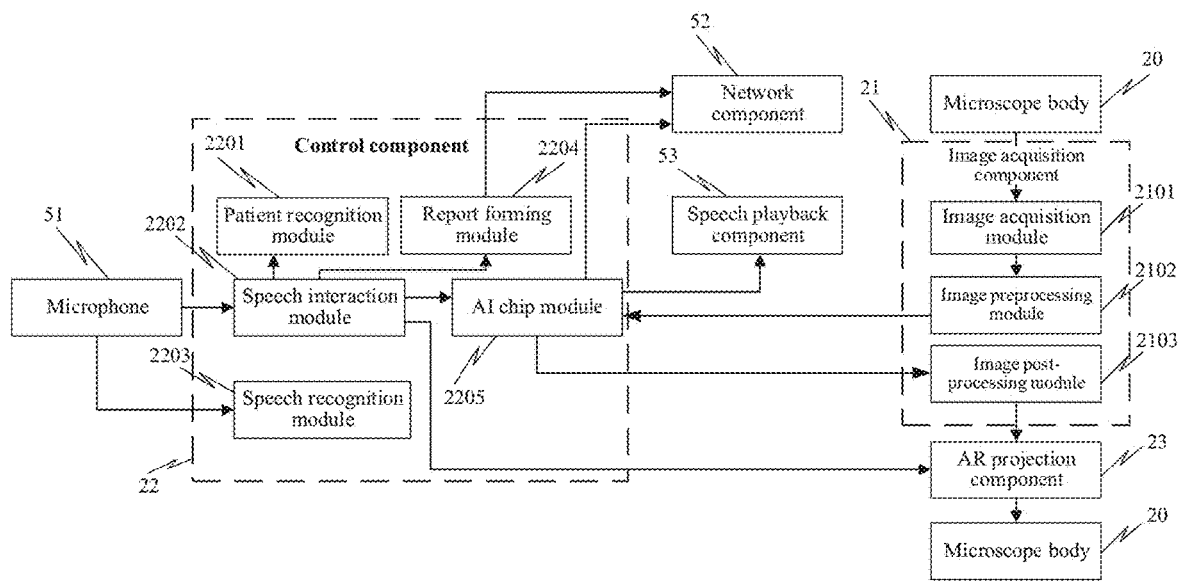
FIG. 20 is a schematic structural diagram of hardware of a pathologic microscope according to an embodiment.

In an embodiment, the pathologic microscope includes an image acquisition component 21, a control component 22, an AR projection component 23, a speech acquisition component 51, a network component 52, and a speech playback component 53. Each component further includes modules or code for implementing functions shown in FIG. 20.

The control component 22 includes a report forming module 2204, a speech interaction module 2202, a speech recognition module 2203, a patient recognition module 2201, and an AI chip module 2205. The image acquisition component 21 includes an image acquisition module 2101, an image preprocessing module 2102, and an image postprocessing module 2103.

A microphone may be used as the speech acquisition component 51. The pathologic microscope acquires, through the microphone 51, a speech signal from a user, the microphone 51 transmits the speech signal to the speech interaction module 2202, and the speech interaction module 2202 generates a control instruction according to the received speech signal from the user. The image acquisition module 2101 acquires a pathological section image on an incident optical path of a microscope body 20, and then the image preprocessing module 2102 performs image preprocessing on the pathological section image to obtain a pathological digital image.

When the control instruction is a model selection instruction, the speech interaction module 2202 generates the model selection instruction, so that the pathological digital image selects a corresponding target AI analysis model according to a use scenario under a command of the model selection instruction. The target AI analysis model is stored in the AI chip module 2205, and AI analysis is performed by using the AI analysis model in the AI chip module 2205 to obtain AI analysis information. The image post-processing module 2103 generates AI analysis information in a projectable form from the AI analysis information in a text form. The AI analysis information in the projectable form is projected to an outgoing optical path of the microscope body 20 by the AR projection component 23.

In some embodiments, the AI chip module performs AI analysis on the pathological digital image by using the AI analysis model to obtain the AI analysis information, and the speech playback component 53 may play the AI analysis information.

The control instruction further includes a first generation instruction and a second generation instruction. When the control instruction is the first generation instruction, the speech interaction module 2202 transmits the first generation instruction to the report forming module 2204, and the report forming module 2204 generates a pathological report according to the first generation instruction. The pathological report includes the AI analysis information. When the control instruction is the second generation instruction, the speech interaction module 2202 transmits the second generation instruction to the report forming module 2204, and the report forming module 2204 generates a case history report according to the second generation instruction, the case history report including the AI analysis information and patient information. The patient information may be any information inputted by a doctor using the speech acquisition component or entered by the patient. The patient information is corresponding information obtained by invoking the patient recognition module 2201 according to the second generation instruction using the speech interaction module 2202 and recognizing a text or a graphic code on a pathological section by using the patient recognition module 2201, or may be further inputted by a doctor by using the speech acquisition component.

The speech recognition module 2203 recognizes a speech signal, and expresses content of the speech signal in a text form corresponding to the speech signal. As such, a doctor may dictate pathological diagnosis through the microphone 51. The speech recognition module 2203 recognizes oral content, expresses the oral content in a text form, where the recognized content is diagnosis content of a pathological report, and generates the pathological report with reference to AI analysis information. Also, a doctor dictates diagnosis through the microphone 51, and the speech recognition module 2203 recognizes oral content, expresses the oral content in a text form, where the recognized content is case history diagnosis content and/or patient information in a case history report, and generates the case history report with reference to AI analysis information.

At least one AI analysis model may be downloaded by using the network component 52, or when a target AI analysis model is not stored in the apparatus, the network component 52 automatically downloads the target AI analysis model. The downloaded AI analysis model or target AI analysis model may be stored in the AI chip module. The pathological section image and/or the pathological digital image and/or the AI pathological section image of the pathologic microscope may be uploaded to a second target device or shared to a preset sharing channel by using the network component 52. In addition, the network component 52 may upload the pathological report and the case history report formed by the report forming module 2204 to a first target device. Specific descriptions of the first target device, the second target device, and the preset sharing channel are described above. Details are not described herein again.

Figure 21:
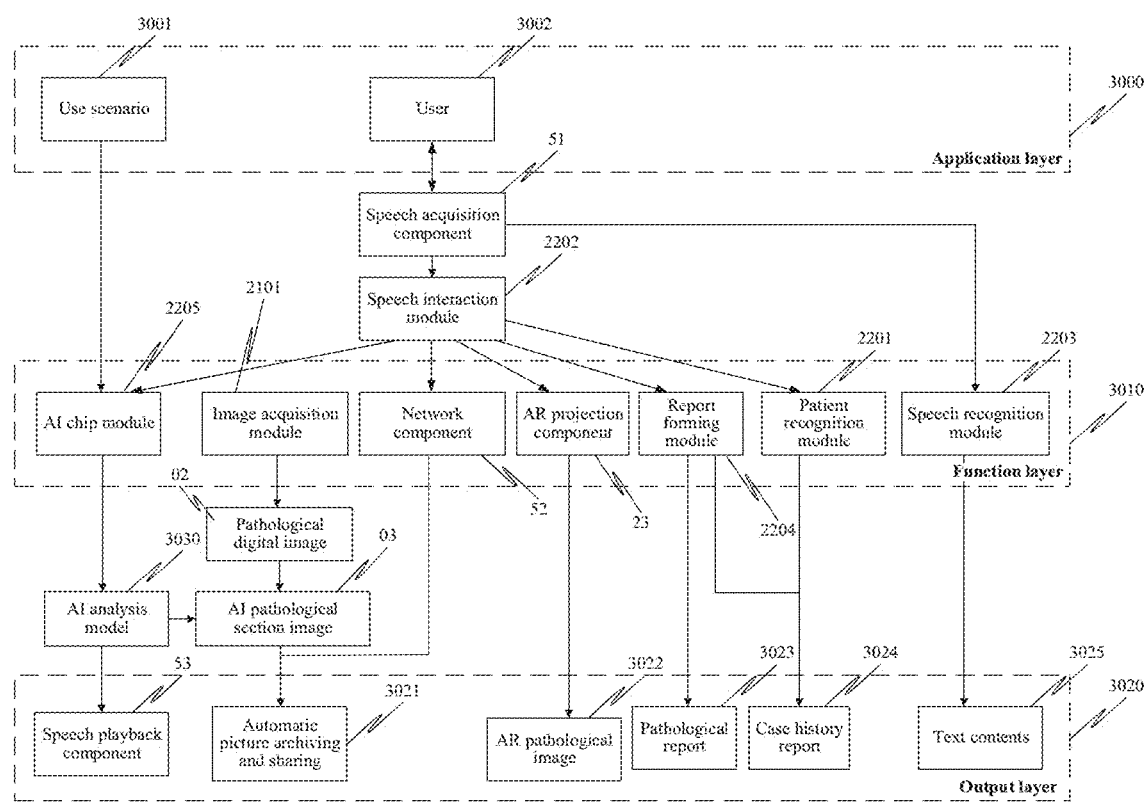
FIG. 21 is an application flowchart of a function of a pathologic microscope according to an embodiment.

In an embodiment, a structure of the pathologic microscope 200 may be divided into an application layer 3000, a function layer 3010, and an output layer 3020 according to a functional structure. As shown in FIG. 21, the application layer 3000 includes a use scenario 3001 and a user 3002. The user 3002 issues a command to a pathologic microscope by using a speech acquisition component 51, and the speech acquisition component 51 acquires an external speech to obtain a speech signal and sends the speech signal to a speech interaction module 2202 for recognition to form or generate a control instruction. The function layer 3010 can be operated and controlled according to different control instructions to control the pathologic microscope.

The function layer 3010 includes an image acquisition module 2101, an AI chip module 2205, a network component 52, an AR projection component 23, a report forming module 2204, a patient recognition module 2201, and a speech recognition module 2203.

The output layer 3020 includes automatic picture archiving and sharing 3021, an AR pathological image 3022, a pathological report 3023, a case history report 3024, a speech playback component 53, and text content 3025.

The image acquisition module 2101 acquires a pathological section image of a pathological section and obtains a pathological digital image after processing. AI analysis is performed on the pathological digital image by using an AI technology, and the speech interaction module 2202 sends a model selection instruction according to the use scenario 3001, selects a corresponding target AI analysis model, and determines an AI analysis model 3030. The AI analysis model 3030 may be stored in the AI chip module 2205. The pathological digital image is processed by the AI analysis model 3030 to obtain an AI pathological section image 03, the automatic picture archiving and sharing 3021 is performed on the AI pathological section image 03 under the speech interaction module 2202 controlling the network component 52.

The AI analysis is performed by using the AI analysis model to obtain AI analysis information, and the AI analysis information may be played by using the speech playback component 53.

The obtained AI pathological section image 03 is controlled by the speech interaction module 2202, the AI analysis information is projected by using the AR projection component 23 to obtain a projected AR pathological image 3022. The AR pathological image 3022 is located on an outgoing optical path of the microscope body. When the control instruction of the speech interaction module 2202 is a first generation instruction, the report forming module 2204 generates the pathological report 3023, the pathological report 3023 including the AI analysis information. When the control instruction of the speech interaction module 2202 is a second generation instruction, the report forming module 2204 generates the case history report 3024, the case history report 3024 including the AI analysis information and patient information. The patient information is obtained by the speech interaction module 2202 controlling the patient recognition module 2201 to invoke and recognize corresponding patient information, and the invoking manner is to recognize a text or a graphic code on a pathological section or complete patient information input through doctor.

The doctor or a user may recognize, by using the speech recognition module 2203, speech content acquired by the speech acquisition component 51, the speech content is recognized into text content, that is, the doctor may complete writing of pathological diagnosis content of the pathological report through dictation, or the doctor may complete at least one of writing of case history diagnosis content of the case history report or input of patient information through dictation.

The control component further controls a speech playback component to play the AI analysis information, so that a process in which a doctor views paper information or electronic information may be avoided, and the doctor only needs to listen to the played information to perform professional diagnosis, thereby improving diagnosis efficiency.

The steps of the embodiments described above are not necessarily performed according to a sequence indicated by step numbers. Unless explicitly indicated, the sequence of the steps is not strictly limited, and the steps may be performed in other sequences. Moreover, at least some of the steps in each embodiment may include a plurality of sub-steps or a plurality of stages. The sub-steps or stages are not necessarily performed at the same moment but may be performed at different moments. Execution of the sub-steps or stages is not necessarily sequentially performed, but may be performed alternately with other steps or simultaneously with at least some of sub-steps or stages of other steps.

A person of ordinary skill in the art may understand that all or some of the processes according to the foregoing embodiments may be implemented by using a computer program to instruct related hardware. The program may be stored in a non-volatile computer-readable storage medium, and the program, when executed, may include the processes of the foregoing embodiments. Any reference to the memory, storage, a database, or other media used in the embodiments may include a non-volatile and/or volatile memory. The non-volatile memory may include a read-only memory (ROM), a programmable ROM (PROM), an electrically programmable ROM (EPROM), an electrically erasable programmable ROM (EEPROM), or a flash memory. The volatile memory may include a random access memory (RAM) or an external cache. As an illustration instead of a limitation, the RAM is available in various forms, such as a Static RAM (SRAM), a Dynamic RAM (DRAM), a Synchronous DRAM (SDRAM), a Double Data Rate SDRAM (DDRSDRAM), an Enhanced SDRAM (ESDRAM). Synchronous link (Synchlink) DRAM (SLDRAM), a Rambus Direct RAM (RDRAM), a Direct Rambus Dynamic RAM (DRDRAM), and a Rambus Dynamic RAM (DRAM).

In addition, the embodiments of the disclosure may be performed or executed by at least one processor. The processor may be implemented in at least one hardware form of a digital signal processor (DSP), a field programmable gate array (FPGA), and a programmable logic array (PLA). The processor 901 may include a main processor and a coprocessor. The main processor is configured to process data in an awake state, also referred to as a central processing unit (CPU), and the coprocessor is a low-power processor configured to process data in a standby state. The processor may further include an artificial intelligence (AI) processor. The AI processor is configured to process a computing operation related to machine learning.

The term "multiple" described throughout the disclosure may refer to two or more. "And/or" describes an association relationship for describing associated objects and represents that at least three relationships may exist. For example, A and/or B may represent only A, both A and B, and only B.

A person of ordinary skill in the art may understand that all or some of steps of the embodiments may be implemented by hardware or a program instructing related hardware. The program may be stored in a computer-readable storage medium. The storage medium may be a read-only memory (ROM), a magnetic disk or an optical disc.

The foregoing descriptions are merely example embodiments of the disclosure, but are not intended to limit the scope of the disclosure. Any modification, equivalent replacement, or improvement made without departing from the spirit and principle of this application falls within the protection scope of the disclosure.

What is claimed is:

1. An apparatus for controlling a pathologic microscope, the apparatus comprising:
    a camera disposed on an incident optical path of the pathologic microscope and configured to acquire a pathological digital image from the incident optical path;
    a microphone configured to acquire a speech signal;
    at least one processor configured to:
        generate a control instruction according to the speech signal and control an analysis process of an artificial intelligence (AI) analysis according to the control instruction;
        select, based on the control instruction being a model selection instruction, a target AI analysis model according to the model selection instruction;
        perform AI analysis on the pathological digital image to generate AI analysis information using the target AI analysis model, the AI analysis comprising:
            determine a tumor area detection AI model as the target AI analysis model based on determining that the pathological digital image relates to a tumor area detection, and execute the tumor area detection AI model to perform the AI analysis on the pathological digital image to obtain tumor analysis information;
            determine a cell detection AI model as the target AI analysis model based on determining that the pathological digital image relates to a cell detection, and execute the cell detection AI model to perform the AI analysis on the pathological digital image to obtain cell detection information; or
            determine an infectious disease detection AI model as the target AI analysis model based on determining that the pathological digital image relates to an infectious disease detection, and execute the infectious disease detection AI model to perform the AI analysis on the pathological digital image to obtain infectious disease detection information; and
    an image projector disposed on an outgoing optical path of the pathologic microscope and configured to project the AI analysis information on a microscopic field of the pathologic microscope on the outgoing optical path.

2. The apparatus according to claim 1, wherein the at least one processor is further configured to:
    obtain at least one AI analysis model;
    determine the target AI analysis model, among the at least one AI analysis model, corresponding to the pathological digital image; and
    execute the target AI analysis model to perform the AI analysis on the pathological digital image to generate the AI analysis information.

3. The apparatus according to claim 2, wherein the at least one processor is further configured to transmit the pathological digital image to a server storing a plurality of AI analysis models and obtain the at least one AI analysis model from the server.

4. The apparatus according to claim 1, further comprising:
a network interface connected to the at least one processor,
wherein the at least one processor is further configured to download at least one AI analysis model through the network interface.

5. The apparatus according to claim 1, further comprising:
the at least one processor is further configured to generate a pathological report based on determining that the control instruction is a first generation instruction, the pathological report comprising the AI analysis information, and
wherein the at least one processor is further configured to generate a case history report based on determining that the control instruction is a second generation instruction, the case history report comprising the AI analysis information and patient information, the patient information being recognized from a text or a graphic code on a pathological section of the pathological digital image.

6. The apparatus according to claim 5, wherein the at least one processor is further configured to recognize the speech signal.

7. The apparatus according to claim 5, further comprising:
a network interface connected to the at least one processor,
wherein the at least one processor is further configured to:
upload, by using the network interface, the pathological report or the case history report to a first target device; and
upload, by using the network interface, a microscope image superimposed on the AI analysis information to a second target device or a preset sharing channel.

8. The apparatus according to claim 1, further comprising:
a speaker connected to the at least one processor,
wherein the at least one processor is further configured to control the speaker to play the AI analysis information.

9. The apparatus according to claim 1, wherein at least one of the camera, the at least one processor, the image projector, the microphone, a network interface, or a speaker is integrated in the pathologic microscope.

10. The apparatus according to claim 1, wherein the pathologic microscope comprises:
a first physical interface formed on a first body part of the pathologic microscope, the first physical interface being used for mounting the camera; and
a second physical interface formed on a second body part of the pathologic microscope, the second physical interface being used for mounting the image projector.

11. A method for controlling a pathologic microscope, the method being performed by at least one processor, and the method comprising:
obtaining a pathological digital image from an incident optical path of pathologic microscope;
acquiring a speech signal;
generating a control instruction according to the speech signal and controlling an analysis process of an artificial intelligence (AI) analysis according to the control instruction;
selecting, based on the control instruction being a model selection instruction, a target AI analysis model according to the model selection instruction;
performing AI analysis on the pathological digital image to generate AI analysis information using the target AI analysis model, on the pathological digital image to generate AI analysis information using the target AI analysis model, the AI analysis comprising:
determine a tumor area detection AI model as the target AI analysis model based on determining that the pathological digital image relates to a tumor area detection, and execute the tumor area detection AI model to perform the AI analysis on the pathological digital image to obtain tumor analysis information;
determine a cell detection AI model as the target AI analysis model based on determining that the pathological digital image relates to a cell detection, and execute the cell detection AI model to perform the AI analysis on the pathological digital image to obtain cell detection information; or
determine an infectious disease detection AI model as the target AI analysis model based on determining that the pathological digital image relates to an infectious disease detection, and execute the infectious disease detection AI model to perform the AI analysis on the pathological digital image to obtain infectious disease detection information; and
controlling an augmented reality (AR) projection component to project the AI analysis information on a microscopic field of the pathologic microscope on an outgoing optical path.

12. The method according to claim 11, wherein the performing the AI analysis on the pathological digital image further comprises:
obtaining at least one AI analysis model;
determining the target AI analysis model, among the at least one AI analysis model, corresponding to the pathological digital image; and
executing the target AI analysis model to perform the AI analysis on the pathological digital image to generate the AI analysis information.

13. The method according to claim 11, further comprising:
based on determining that the control instruction is a first generation instruction, generating a case history report comprising the AI analysis information; and
based on determining that the control instruction is a second generation instruction, generating the case history report comprising the AI analysis information and patient information, the patient information being recognized from a text or a graphic code on a pathological section of the pathological digital image.

14. The method according to claim 13, further comprising:
recognizing the speech signal.

15. The method according to claim 13, further comprising:
uploading, through a network interface, the a case history report or the case history report to a first target device; and
uploading, through the network interface, a microscope image superimposed on the AI analysis information to a second target device or a preset sharing channel.

16. A non-transitory computer-readable storage medium storing computer program code to cause at least one computer processor to:
obtain a pathological digital image from an incident optical path of a pathologic microscope;
acquire a speech signal;
generate control instruction according to the speech signal and control an analysis process of an artificial intelligence (AI) analysis according to the control instruction;

select, based on the control instruction being a model selection instruction, a target AI analysis model according to the model selection instruction;

perform AI analysis on the pathological digital image to generate AI analysis information using a target AI analysis model, the AI analysis comprising:

determine a tumor area detection AI model as the target AI analysis model based on determining that the pathological digital image relates to a tumor area detection, and execute the tumor area detection AI model to perform the AI analysis on the pathological digital image to obtain tumor analysis information;

determine a cell detection AI model as the target AI analysis model based on determining that the pathological digital image relates to a cell detection, and execute the cell detection AI model to perform the AI analysis on the pathological digital image to obtain cell detection information; or determine an infectious disease detection AI model as the target AI analysis model based on determining that the pathological digital image relates to an infectious disease detection, and execute the infectious disease detection AI model to perform the AI analysis on the pathological digital image to obtain infectious disease detection information; and control an augmented reality (AR) projection component to project the AI analysis information on a microscopic field of the pathologic microscope on an outgoing optical path.

* * * * *